United States Patent
Priebe et al.

(10) Patent No.: US 11,925,654 B2
(45) Date of Patent: *Mar. 12, 2024

(54) ESTERS OF 2-DEOXY-MONOSACCHARIDES WITH ANTI PROLIFERATIVE ACTIVITY

(71) Applicant: Board of Regents, The University of Texas System, Austin, TX (US)

(72) Inventors: Waldemar Priebe, Houston, TX (US); Marcin Cybulski, Warsaw (PL); Izabela Fokt, Houston, TX (US); Stanislaw Skora, Houston, TX (US); Charles Conrad, Austin, TX (US); Timothy Madden, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 50 days.

This patent is subject to a terminal disclaimer.

(21) Appl. No.: 17/339,028

(22) Filed: Jun. 4, 2021

(65) Prior Publication Data
US 2022/0023326 A1    Jan. 27, 2022

Related U.S. Application Data

(63) Continuation of application No. 16/229,338, filed on Dec. 21, 2018, now Pat. No. 11,026,960, which is a continuation of application No. 14/782,521, filed as application No. PCT/US2014/032942 on Apr. 4, 2014, now Pat. No. 10,201,554.

(60) Provisional application No. 61/809,110, filed on Apr. 5, 2013.

(51) Int. Cl.
*A61K 31/7024*    (2006.01)
*A61P 35/00*    (2006.01)
*A61P 35/04*    (2006.01)

(52) U.S. Cl.
CPC .......... *A61K 31/7024* (2013.01); *A61P 35/00* (2018.01); *A61P 35/04* (2018.01)

(58) Field of Classification Search
CPC .................................................. A61K 31/7024
See application file for complete search history.

(56) References Cited

U.S. PATENT DOCUMENTS

| | | | |
|---|---|---|---|
| 4,464,530 | A | 8/1984 | Matsumura |
| 5,833,960 | A | 11/1998 | Gers Barlag |
| 6,319,695 | B1 | 11/2001 | Wong |
| 6,670,330 | B1 | 12/2003 | Lampidis |
| 6,894,033 | B2 | 5/2005 | Cruz |
| 6,906,048 | B2 | 6/2005 | Davis |
| 6,979,675 | B2 | 12/2005 | Tidmarsh |
| 7,001,888 | B2 | 2/2006 | Tidmarsh |
| 8,299,033 | B2 | 10/2012 | Priebe |
| 8,927,506 | B2 | 1/2015 | Priebe |
| 9,149,489 | B2 | 10/2015 | Priebe |
| 10,201,554 | B2 | 2/2019 | Priebe |
| 11,026,960 | B2 | 6/2021 | Priebe |
| 2002/0045597 | A1 | 4/2002 | Anastassiades |
| 2004/0138143 | A1 | 7/2004 | Glombik |
| 2004/0167079 | A1 | 8/2004 | Tidmarsh |
| 2005/0043250 | A1 | 2/2005 | Lampidis |
| 2005/0143336 | A1 | 6/2005 | Ramesh |
| 2006/0025351 | A1 | 2/2006 | Lampidis |
| 2007/0292478 | A1 | 12/2007 | Youri |
| 2009/0305997 | A1 | 12/2009 | Pineau |
| 2010/0130434 | A1 | 5/2010 | Priebe |
| 2010/0152121 | A1 | 6/2010 | Priebe |
| 2011/0003758 | A1 | 1/2011 | Priebe |
| 2011/0160151 | A1 | 6/2011 | Priebe |
| 2012/0276108 | A1 | 11/2012 | Priebe |

FOREIGN PATENT DOCUMENTS

| | | |
|---|---|---|
| EP | 1881000 | 1/2008 |
| JP | 56103197 A | 8/1981 |
| JP | 2006515883 A | 6/2006 |
| WO | 1997000882 | 1/1997 |
| WO | 2001082926 | 11/2001 |
| WO | 2003018598 | 3/2003 |
| WO | 2004108166 | 12/2004 |
| WO | 2007000882 | 1/2007 |
| WO | 2007100728 | 9/2007 |
| WO | 2007101148 | 9/2007 |
| WO | 2008131024 | 10/2008 |
| WO | 2009108926 | 9/2009 |
| WO | 2010005799 | 1/2010 |
| WO | 2012097052 | 7/2012 |
| WO | 2012142615 | 10/2012 |

OTHER PUBLICATIONS

Adam, M. et al., "Synthesis and Preliminary Evaluation of ['☐F]2deoxy ☐2,2☐difluoro☐glucose as a Potential PET Imaging Agent", J Labelled Cpd Radiopharm., 42(8):809-13, (1999).

Adamson, J. et al., "Preliminary Communication 2-Deoxy-2,2-difluoro-D-arabino-hexose ("2,2-difluoroglucose")", Carbohyd Res., 18(2)345-7, (1971).

Aft, R. et al., "Enhancing Targeted Radiotherapy by Copper(II)Diacetyl-bis(N☐-methylthiosemicarbazone) Using 2-Deoxy-D-glucose", Cancer Res., 63(17):5496-504, (2003).

Altan, N. et al., "Defective Acidification in Human Breast Tumor Cells and Implications for Chemotherapy", J Exp Med, 187(10):1583-98, (1998).

Beer, T. et al., "Calcitriol in Cancer Treatment: From the Lab to the Clinic", Mol Cancer Ther., 3(3):373-81, (2004).

Beis,I., et al., The Contents of Adenine Nucleotides, Phosphagens and some Glycolytic Intermediates in Resting Muscles from Vertebrates and Invertebrates, Biochem. J. 152, 23-32, (1975).

Bessel, E. et al., "Some In Vivo and In Vitro Antitumour Effects of the Deoxyfluoro-D-gluco-phyranoses", Eur J Cancer, 9(7):463-70, (1973).

(Continued)

*Primary Examiner* — Bahar Craigo
(74) *Attorney, Agent, or Firm* — Cynthia Hathaway; Lauren L. Stevens; Erik M. Larsen

(57) ABSTRACT

Compounds and methods of using the same to inhibit glycolysis and treat cancer and other diseases are disclosed.

32 Claims, 1 Drawing Sheet

(56) References Cited

OTHER PUBLICATIONS

Bessel, E. et al., "The Use of Deoxyfluoro-D-glucopyranoses and Related Compounds in A Study of Yeast Hexokinase Sepcficity", Biochem J., 128(2):199-204, (1972).
Bursch, W. et al., "Programmed Cell Death (PCD). Apoptosis, Autophagic PCD, or Others?", Ann N Y Acd Sci., 926:1-12, (2000).
CN Application No. 200980135924; Office Action and Search Report, dated Dec. 27, 2012; 6 pages.
CN Application No. 200980135924; Office Action, dated Jan. 29, 2012; 6 pages.
Costantino, V. et al., "A Mild and Easy One-Pot Procedure for the Synthesis of 2-deoxysugars From Glycals", Tetrahedron Letters, 41(47):9177-80, (2000).
Cuervo, A., "Autophagy: In Sickness and in Health", Trends Cell Biol., 14(2):70-7, (2004).
Daido, S. et al., "Inhibition of the DNA-Dependent Protein Kinase Catalytic Subunit Radiosensitizes Malignant Glioma Cells by Inducing Autophagy", Cancer Res., 65(10):4368-75, (2005).
Danishefsky, S. et al., "The Total Synthesis of Avermectin A1a. New Protocols for the Synthesis of Novel 2-deoxypyranose Systems and Their Axial Glycosides", J Am Chem Soc., 109(26):8119-20, (1987).
Edinger, A. et al., "Defective Autophagy Leads to Cancer", Cancer Cell, 4(6):422-4, (2003).
EP Application No. 09794965.5; Extended Supplementary Search Report and Search Opinion, dated Mar. 22, 2012; 5 pages.
Finch, P. et al., "The Substrate Specificity of Yeast Hexokinase: Reaction with D-Arabinose Oxime", Carbohydr Res., 76:225-32, (1979).
Fleming, J. et al., "Molecular Consequences of Silencing Mutant K-ras in Pancreatic Cancer Cells: Justification for K-ras-Directed Therapy", Mol Cancer Res., 3(7):413-23, (2005).
Fowler, J. et al., "Agents for the Armamentarium of Regional Metabolic Measurement In Vivo Via Metabolic Trapping-C-11-2-Deoxy-D-glucose and Halogenated Deoxyglucose Derivatives", J Labelled Cpd Radiopharma., 16(1):7-9, (1979).
Garber, K., "Energy Boost: The Warburg Effect Returns in a New Theory of Cancer", J Natl Cancer Inst., 96(24):1805-6, (2004).
Gatenby, R. et al., "Why Do Cancers Have High Aerobic Glycolysis?", Nat Rev Cancer, 4(11):891-9, (2004).
Gatley, S., "Labeled Glucose Analogs in the Genomic Era", J Nucl Med., 44(7):1082-6, (2003).
Gould, G. et al., "Expression of Human Glucose Transporters in Xenopus Oocytes: Kinetic Characterization and Substrate Specificities of the Erythrocyte, Liver, and Brain Isoforms", Biochemistry, 30(21):5139-45, (1991).
Gove, P. et al., Webster's Third New International Dictionary, p. 1798, (1963).
Gozuacik, D. et al., "Autophagy as a Cell Death and Tumor Suppressor Mechanism", Oncogene, 23(16):2891-906, (2004).
Greene, T. et al., "Protection for the Hydroxyl Group, Including 1,2- and 1,3-diols", Prot Groups Org Synth., Third Edition, 48 pages, (1999).
Hait, W. et al., "A Matter of Life or Death (or Both): Understanding Autophagy in Cancer", Clin Cancer Res., 12(7):1961-5, (2006).
Hennen W. et al., "Enzymes in Carbohydrate Synthesis: Lipase-Catalyzed Selective Acylation and Deacylation of Furanose and Pyranose Derivatives", J Org Chem., 53:4939-45, (1988).
Huang, X et al., 'Hydrolysis of (2-Deoxy-beta-D-glucopyranosyl)pyridinium Salts', J. Am. Chem. Soc., (1995), vol. 117, No. 43, pp. 10614-10621, XP008141802.
International Application No. PCT/US2008/060511; International Preliminary Report on Patentability, dated Oct. 20, 2009; 5 pages.
International Application No. PCT/US2008/060511; Written Opinion of the International Searching Authority, dated Jul. 14, 2008; 4 pages.
International Application No. PCT/US2009/048675; International Preliminary Report on Patentability, dated Jan. 11, 2011; 5 pages.
International Application No. PCT/US2009/048675; International Search Report and Written Opinion of the International Searching Authority, dated Mar. 3, 2010; 8 pages.
International Application No. PCT/US2009/35702; International Preliminary Report on Patentability, dated Aug. 31, 2010; 4 pages.
International Application No. PCT/US2009/35702; International Search Report and Written Opinion of the International Searching Authority, dated May 5, 2009; 5 pages.
International Application No. PCT/US2012/020920; International Preliminary Report on Patentability, dated Jul. 16, 2013; 7 pages.
International Application No. PCT/US2012/020920; International Search Report and Written Opinion of the International Searching Authority, dated Jul. 2, 2012; 11 pages.
International Application No. PCT/US2012/033837; International Search Report and Written Opinion of the International Searching Authority, dated Nov. 29, 2012; 9 pages.
International Application No. PCT/US2014/032942; International Preliminary Report on Patentability, dated Oct. 6, 2015; 8 pages.
International Application No. PCT/US2014/032942; International Search Report and Written Opinion of the International Searching Authority, dated Sep. 26, 2014; 12 pages.
Kabeya, Y. et al., "LC3, a Mammalian Homologue of Yeast Apg8p, Is Localized in Autophagosome Membranes After Processing", EMBO J, 19(21):5720-8, (2000).
Kanzawa, T. et al., "Induction of Autophagic Cell Death in Malignant Glioma Cells by Arsenic Trioxide", Cancer Res., 63(9):2103-8, (2003).
Kim, N. et al., "Auranofin blocks interleukin-6 signalling by inhibiting phosphorylation of JAK1 and STAT3", Immunology, 122(4):607-14, (2007).
Klionsky, D. et al., "Autophagy as a Regulated Pathway of Cellular Degradation", Science, 290(5497):1717-21, (2000).
Kojima, M. et al., "Metabolic Pathway of 2-Deoxy-2-Fluoro-D-Glucose and 2-Deoxy-2-Fluoro-D-Mannose in Mice Bearing Sarcoma 180 Studied by Fluorine-19 Nuclear Magnetic Resonance", Chem Pharm Bull., 36(3):1194-7, (1988).
Kondo, Y. et al., "Role of Autophagy in Cancer Development and Response to Therapy", Nat Rev Cancer, 5(9):726-34, (2005).
Kurtoglu, M. et al., "Under normoxia, 2-deoxy-D-glucose elicits cell death in select tumor types not by inhibition of glycolysis but by interfering with N-linked glycosylation", Mol Cancer Ther., 6(11):3049-58, (2007).
Lampidis, T. et al., "Efficacy of 2-halogen Substituted D-glucose Analogs in Blocking Glycolysis and Killing Hypoxic Tumor Cells", Cancer Chemother Pharmacol., 58(6):725-34, (2006).
Lampidis, T. et al., "Growth Inhibitory Effects of 2-halo Analogs of 2-deoxy-D-glucose on Hypoxic Tumor Cells", Abstract Submission, Control No. 04-AB-4359-AACR, (2003).
Liang, X. et al., "Induction of Autophagy and Inhibition of Tumorigenesis by Beclin 1", Nature, 402(6762):672-6, (1999).
Liu, K. et al., "Enzymatic Halohydration of Glycals", J Org Chem., 57(13):3748-50, (1992).
Lu, H. et al., "Hypoxia-inducible Factor 1 Activation by Aerobic Glycolysis Implicates the Warburg Effect in Carcinogenesis", J Bio Chem., 277(26):23111-5, (2002).
Malaisse, W. et al., "Cytotoxic Action of 2-deoxy-D-glucose Tetraacetate in Tumoral Pancreatic Islet Cells", Cancer Lett., 125(1-2):45-9, (1998).
Mccarter, J. et al., "Syntheses, Radiolabelling, and Kinetic Evaluation of 2-deoxy-2-fluoro-2-iodo-D-hexoses for Medical Imaging", Carbohydr Res., 266(2):273-7, (1995).
MERCK Manual Online Edition, "Brain Tumor", retrieved on May 11, 2011, from http://www.merckmanuals.com/home/print/sec06/ch088/ch088b.html, (revision 2008).
MERCK Manual Online Edition, "Cancer Treatment Principles", retrieved on Feb. 21, 2011, from http://www.merckmanuals.com/, (revision 2007).
Mizushima, N. et al., "Dissection of Autophagosome Formation Using Apg5-Deficient Mouse Embryonic Stem Cells", J Cell Biol., 152(4):657-68, (2001).
Mohanti, B. et al., "Improving Cancer Radiotherapy with 2-deoxy-D-glucose: Phase I/II Clinical Trials on Human Cerebral Gliomas", Int J Radiat Oncol Biol Phys., 35(1):103-11, (1996).
Morin, C., "Procurement of 2-deoxy-2-iodo-D-glucose (2-DIG)", Tetrahedron Letters, 47:5055-8, (2006).

(56) References Cited

OTHER PUBLICATIONS

Munafó, D. et al., "A Novel Assay to Study Autophagy: Regulation of Autophagosome Vacuole Size by Amino Acid Deprivation", J Cell Sci., 114(Pt 20):3619-29, (2001).
Oconnell, T. et al., "Identification of 2-fluoro-2-deoxy-D-glucose Metabolites by 19F(1H) hetero-Relay", J Magn Reson B, 109(3):264-9, (1995).
Ogier-Denis, E. et al., "Autophagy: A Barrier or an Adaptive Response to Cancer", Biochim Biophys Acta, 1603(2):113-28, (2003).
Paglin, S. et al., "A Novel Response of Cancer Cells to Radiation Involves Autophagy and Formation of Acidic Vesicles", Cancer Res., 61(2):439-44, (2001).
Pelicano, H. et al., "Glycolysis Inhibition for Anticancer Treatment", Oncogene, 25(34):4633-46, (2006).
Pulido, R. et al., "Towards the Selective Acylation of Secondary Hydroxyl Groups of Carbohydrates Using Oximeestersin", Carbohydr Res., 252:55-68, (1994).
Qu, X. et al., "Promotion of Tumorigenesis by Heterozygous Disruption of the Beclin 1 Autophagy Gene", J Clin Invest., 112(12):1809-20, (2003).
Roush, W. et al., "2-Deoxy-2-iodo-alpha-mannopyranosyl and -Talopyranosyl Acetates: Highly Stereoselective Glycosyl Donors for the Synthesis of 2-deoxy-alpha-glycosides", Org Lett., 1(6):899-902, (1999).
Shintani, T. et al., "Autophagy in Health and Disease: A Double-Edged Sword", Science, 306(5698):990-5, (2004).
Takeuchi, H. et al., "Synergistic Augmentation of Rapamycin-Induced Autophagy in Malignant Glioma Cells by Phosphatidylinositol 3-Kinase/Protein Kinase B Inhibitors", Cancer Res., 65(8):3336-46, (2005).
U.S. Appl. No. 12/581,550; Final Office Action, dated Mar. 6, 2012; 13 pages.
U.S. Appl. No. 12/581,550; Non-Final Office Action, dated May 27, 2011; 20 pages.
U.S. Appl. No. 12/581,550; Notice of Allowance, dated Jul. 23, 2012; 9 pages.
U.S. Appl. No. 12/920,104; Final Office Action, dated Apr. 18, 2014; 11 pages.
U.S. Appl. No. 12/920,104; Final Office Action, dated Jan. 7, 2013; 11 pages.
U.S. Appl. No. 12/920,104; Non-Final Office Action, dated Jun. 15, 2012; 9 pages.
U.S. Appl. No. 12/920,104; Notice of Allowance, dated Jan. 23, 2015; 8 pages.
U.S. Appl. No. 12/920,104; Notice of Allowance, dated May 27, 2015; 8 pages.
U.S. Appl. No. 13/003,429; Applicant-Initiated Interview Summary, dated Jan. 30, 2013; 3 pages.
U.S. Appl. No. 13/003,429; Final Office Action, dated Apr. 16, 2013; 6 pages.
U.S. Appl. No. 13/003,429; Non-Final Office Action, dated Jan. 30, 2014; 6 pages.
U.S. Appl. No. 13/003,429; Non-Final Office Action, dated Sep. 26, 2012; 8 pages.
U.S. Appl. No. 13/003,429; Notice of Allowance, dated Sep. 2, 2014; 5 pages.
U.S. Appl. No. 13/347,968; Examiner-Initiated Interview Summary, dated Jun. 5, 2014; 1 page.
U.S. Appl. No. 13/347,968; Non-Final Office Action, dated Nov. 4, 2013; 18 pages.
U.S. Appl. No. 14/782,521; Examiner-Initiated Interview Summary, dated Sep. 27, 2018; 2 pages.
U.S. Appl. No. 14/782,521; Non-Final Office Action dated Dec. 1, 2017; 12 pages.
U.S. Appl. No. 14/782,521; Notice of Allowance, dated Sep. 27, 2018; 22 pages.
U.S. Appl. No. 16/229,338; Final Office Action, dated Oct. 22, 2020; 14 pages.
U.S. Appl. No. 16/229,338; Non-Final Office Action, dated Feb. 14, 2020; 19 pages.
US DHHS Booklet, "What You Need To Know About Cancer of the Pancreas", National Cancer Institute, National Institutes of Health, 48 pages, (2010).
Yang, S. et al., "Further Metabolic Studies of Indole and Sugar Derivatives Using the Staurosporine Producer Streptomyces Staurosporeus", J Nat Prod., 60(3):230-5, (1997).
Yue, Z. et al., "Beclin 1, an Autophagy Gene Essential For Early Embryonic Development, Is a Haploinsufficient Tumor Suppressor", Proc Natl Acad Sci USA, 100(25):15077-82, (2003).

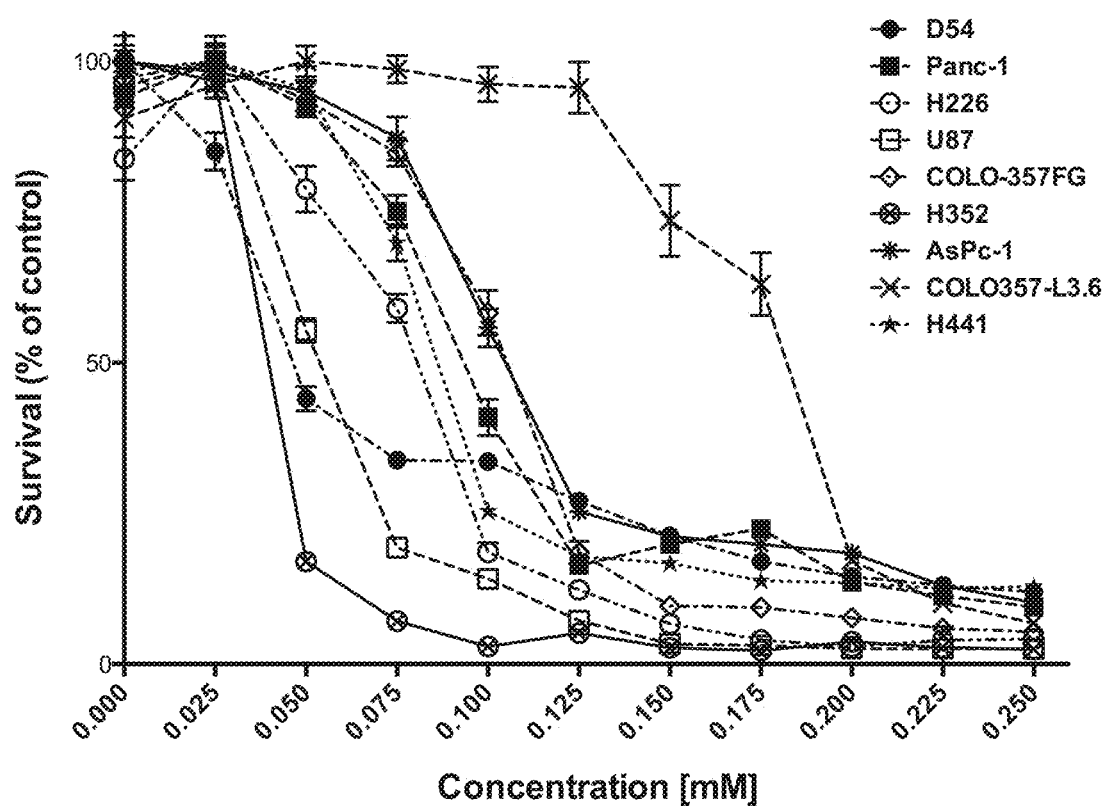
| Cell line | D54 | U87 | Panc-1 | AsPc-1 | Colo357-FG | Colo357-L3.6 | H226 | H352 | H441 |
|---|---|---|---|---|---|---|---|---|---|
| IC50 [µM] | 55.2 | 53.7 | 94.5 | 107.9 | 102.5 | 176 | 76.1 | 39.7 | 87.8 |

ESTERS OF 2-DEOXY-MONOSACCHARIDES WITH ANTI PROLIFERATIVE ACTIVITY

This application is a continuation of U.S. patent application Ser. No. 16/229,338, filed Dec. 21, 2018, which is a continuation of U.S. patent application Ser. No. 14/782,521, filed Feb. 16, 2016, which is a national stage entry under 35 U.S.C. § 371 of International Application No. PCT/US2014/032942, filed Apr. 4, 2014, which claims the benefit of priority of U.S. Provisional Application No. 61/809,110, filed Apr. 5, 2013. The disclosures of which are incorporated by reference as if written herein in their entireties.

The present disclosure relates to highly potent 2-deoxymonosacharide esters and compositions, and to methods of treating tumor cell growth and inflammatory and/or proliferative dermatological diseases.

Reliance on glycolysis has been correlated with disease progression in cancer, and as well as a consistent and significant increase in activity of hexokinase, phosphofructokinase and pyruvate kinase. Hypoxia is also a feature of many solid cancers and has been linked to malignant transformation, metastasis and treatment resistance. Furthermore, glycolysis in cancer cells can be enhanced by certain oncogenes through the increased expression of glucose transporters and glycolytic enzymes found on tumor cells.

Accordingly, the glycolytic pathway has become a potential target for the selective inhibition of many tumor cells. The inhibition of glycolysis would be selective for such tumor cells because normal cells in aerobic conditions would be able to survive such inhibition by generating energy through other pathways (e.g., the Krebs cycle, and oxidative phosphorylation). By contrast, when glycolysis is blocked in glycolytic tumor cells, the tumor cells would die because of an inability to utilize the aforementioned pathways.

However, current glycolytic inhibition approaches for cancer treatment present various challenges. For instance, many such treatments are not specific for the hypoxic environment of tumor cells. More importantly, current treatments are not selective inhibitors of glycolysis. Rather, such treatments can also target other pathways that are essential for normal cell function, such as glycosylation, where monosaccharides such as D-mannose form a part of oligosaccharides linked to proteins to form glycoproteins. Among other functions, glycoproteins are essential for maintaining the structural integrity of cell membranes. Thus, interference with glycosylation can have clinical consequences that may result in beneficial effects in the treatment of inflammatory and proliferative dermatological diseases as well.

Additionally, research suggests short-chain fatty acids (SCFA's) have antiproliferative, apoptotic and differentiating properties as well as can act as inhibitors of histone deacetylases (HDAC). Various SCFA are linked to the degree of induced histone hyperacetylation is produced via anaerobic bacterial fermentation within the colon and is thought to be protective in regard to colon carcinogenesis. Although butyrate (C4) is considered the most potent of the SCFA, a variety of other SCFA also exist in the colonic lumen. Butyrate is thought to exert its cellular effects through the induction of histone hyperacetylation. Propionate (C3) and valerate (C5) caused growth arrest and differentiation in human colon carcinoma cells. In addition, valproic acid has also been suggested to induce cell differentiation, growth arrest, and apoptosis mediated by its histone deacetylases (HDAC)-inhibiting properties.

Thus, there remains a need for improved methods and compositions for treating proliferative diseases, including cancer and inflammatory dermatological diseases.

Accordingly, the inventors herein disclose new methods and compositions for treating proliferative or inflammatory diseases.

Thus, in various embodiments, the present invention provides a method of treating a proliferative or inflammatory disease in a patient in need thereof comprising administering a therapeutically effective amount of one or more compounds of the Formula I:

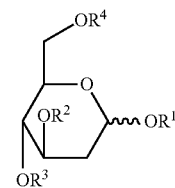

or a salt, ester or prodrug thereof, wherein each $R^1$, $R^2$, $R^3$ and $R^4$ are independently H, or $COR^5$; wherein each $R^5$ is independently selected from the group $C_1$-$C_{10}$ straight- or branched-chain alkyl, $C_4$-$C_{10}$ alkylcycloalkyl, and $C_3$-$C_{10}$ cycloalkyl.

In certain embodiments, $R^2$ and $R^3$ are $COR^5$. In certain embodiments, $R_5$ is independently selected from the group $C_3$-$C_7$ straight- or branched-chain alkyl, $C_4$-$C_{10}$ alkylcycloalkyl, and $C_3$-$C_7$ cycloalkyl. In particular embodiments, the compounds are selected from those illustrated in Table 1.

In various embodiments, the proliferative disease is cancer. In certain embodiments, the cancer is brain, lung, breast, colorectal, prostate, gastric, esophageal, colon, pancreatic, ovarian, and/or hematologic cancer. In particular embodiments, the cancer is glioblastoma, high-grade glioma, and metastatic brain cancer.

BRIEF DESCRIPTION OF THE DRAWINGS

FIG. 1 shows in vitro dose-response activity for Compound WP1234 in D54, U87, Panc-1, AsPc-1, Colo357-FG, Colo357-L3.6, H226, H352, H441 cell lines, and corresponding $IC_{50}$ values.

DETAILED DESCRIPTION OF THE INVENTION

Abbreviations and Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% from the specified amount.

The term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

The term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma cancers, lung cancers, breast cancers, colorectal cancers, prostate cancers, gastric cancers, esophageal cancers, colon cancers, pancreatic cancers, ovarian cancers, or hematologic malignancies.

As used herein, the term "inflammatory disease" or "inflammatory disorder" refers to pathological states resulting in inflammation, typically caused by neutrophil chemotaxis. Examples of such disorders include inflammatory skin diseases including psoriasis and atopic dermatitis.

The fatty acids that can be used in accordance with the present invention comprise a hydrocarbyl portion and a carboxylic acid portion. As used herein, the term "hydrocarbyl" is understood to include "aliphatic," "cycloaliphatic," and "aromatic." The hydrocarbyl groups are understood to include alkyl, alkenyl, alkynyl, cycloalkyl, aryl, aralkyl, and alkaryl groups. Further, "hydrocarbyl" is understood to include both non-substituted hydrocarbyl groups, and substituted hydrocarbyl groups, with the latter referring to the hydrocarbon portion bearing additional substituents, besides carbon and hydrogen. Additionally, while "carboxylic acid" is used to refer to the compounds, salts of such acids, i.e., carboxylates, are also expressly contemplated. Moreover, carboxylic acids and carboxylates may be used interchangeably herein.

In particular, fatty acids include, but are not limited to, those having chain lengths comparable to an unbranched fatty acid of from about 3 carbons to about 14 carbons in length. Thus, the chains can be, for example, from about 3, 4, 5, 6, 7, 8, 9, 10, 11, 12, or 13 carbons in length. The chains can be up to, for example, about 14, 13, 12, 11, 9, 8, 7, 6, 5, or 4 carbons in length. The fatty acids can be straight or branched and can include single, double, and/or triple bonds. Nonlimiting examples of fatty acids include valproate, butyrate, phenylacetate, and phenylbutyrate.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that FIGURE as well, taking into account significant FIGURES.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH3 group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH2-). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C amido" as used herein, alone or in combination, refers to a C(O)N(RR') group with R and R' as defined herein or as defined by the specifically enumerated "R" groups designated. The term "N amido" as used herein, alone or in combination, refers to a RC(O)N(R') group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH3C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O carbamyl" as used herein, alone or in combination, refers to a OC(O)NRR', group with R and R' as defined herein.

The term "N carbamyl" as used herein, alone or in combination, refers to a ROC(O)NR' group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF2-), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of 0, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO2.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2-.

The term "sulfonamido" as used herein refers to a compound group comprising a sulfonyl group and an amino group, which may be a terminal substituent or appear in the middle of a chain. The term "N sulfonamido" refers to a —N(R)S(O)$_2$R' group, and "S sulfonamido" refers to a —S(O)$_2$NRR' group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N thiocarbamyl" refers to an ROC(S)NR'— group, with R and R' as defined herein.

The term "O thiocarbamyl" refers to a —OC(S)NRR', group with R and R' as defined herein.

The term "thiocyanato" refers to a —CNS group.

The term "trihalomethanesulfonamido" refers to a X3CS(O)2NR— group with X is a halogen and R as defined herein.

The term "trihalomethanesulfonyl" refers to a X3CS(O)2- group where X is a halogen.

The term "trihalomethoxy" refers to a X3CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, SCH3, C(O)CH3, CO2CH3, CO2H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R_n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Glycolysis inhibitor" is used herein to refer to a compound that exhibits an IC50 with respect to glycolytic activity or anticancer activity of no more than about 100 µM and more typically not more than about 50 µM, as measured in the assay name described generally herein below. "IC50" is that concentration of inhibitor that reduces the activity of glycolysis to half-maximal level. Certain compounds disclosed herein have been discovered to exhibit inhibition against glycolysis. In certain embodiments, compounds will exhibit an IC50 with respect to glycolysis of no more than about 10 µM; in further embodiments, compounds will exhibit an IC50 with respect to glycolysis of no more than about 5 µM; in yet further embodiments, compounds will exhibit an IC50 with respect to glycolysis of not more than about 1 µM; in yet further embodiments, compounds will exhibit an IC50 with respect to glycolysis of not more than about 200 nM, as measured in the glycolysis assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations that can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation or proliferation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients that can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example, a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example, those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Alternatively, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with cell differentiating agents, anti-proliferative agents, mitochondrial inhibitors, topical steroids, immunosuppressive compounds, JAK2 inhibitors, JAK3 inhibitors, STAT3 inhibitors, STAT5 inhibitors, HIF-1α inhibitors, parathyroid hormone-related protein (PTHrP) agonists, cell adhesion blockers, non-steroidal anti-inflammatory agents, antibacterial agents, alkylating agents, anti-metabolite agents, mitotic inhibitors, tyrosine kinase inhibitors, topoisomerase inhibitors, cancer immunotherapy monoclonal antibodies, anti-tumor antibiotic agents, anti-cancer agents, autophagy-inducing agents, anti-psoriasis drugs, D-mannose, and combinations thereof.

In certain embodiments, cell differentiating agents include, but are not limited to retinoic acid, retinol, retinal, isotretinoin alitretinoin, etretinate, acitretin, tazarotene, bexarotene, adapalene, vitamin D, alfacalcidol (1-hydroxycholecalciferol), calcitriol (1,25-dihydroxycholecalciferol), cholecalciferol (vitamin D3), dihydrotachysterol (DHT) and ergocalciferol (vitamin D2), phorbol esters, and 12-O-tetradecanoylphorbol-13-acetate.

In certain embodiments, mitochondrial inhibitors include, but are not limited to, anthraline, dithranol, chrysarobin, and coal tar.

In certain embodiments, topical steroids include, but are not limited to, clobetasol propionate, betamethasone, betamethasone dipropionate, halobetasol propionate, fluocinonide, diflorasone diacetate, mometasone furoate, halcinonide, desoximetasone, fluticasone propionate, flurandrenolide, triamcinolone acetonide, fluocinolone acetonide, hydrocortisone, hydrocortisone valerate, prednicarbate, desonide, and alclometasone dipropionate.

In certain embodiments, immunosuppressive compounds include, but are not limited to, fingolimod, cyclosporine A, azathioprine, dexamethasone, tacrolimus, sirolimus, pimecrolimus, mycophenolate salts, everolimus, basiliximab, daclizumab, anti-thymocyte globulin, anti-lymphocyte globulin, CTLA4IgG, D-penicillamine, gold salts, hydroxychloroquine, leflunomide, methotrexate, minocycline, sulfasalazine, cyclophosphamide, etanercept, infliximab, adalimumab, anakinra, rituximab, and abatacept.

In certain embodiments, JAK2 inhibitors include, but are not limited to, INCBI8424.

In certain embodiments, JAK3 inhibitors include, but are not limited to, CP-690,550.

In certain embodiments, STAT3 inhibitors include, but are not limited to, WP1066, WP1193, WP1130, and WP1220/MOL4239.

In certain embodiments, STAT5 inhibitors include, but are not limited to, WP1220/MOL4239.

In certain embodiments, parathyroid hormone-related protein (PTHrP) agonists include, but are not limited to, PTH(1-34).

In certain embodiments, cell adhesion blockers include, but are not limited to, bimosiamose.

In certain embodiments, non-steroidal anti-inflammatory agents include, but are not limited to, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, lumiracoxib, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin.

In certain embodiments, antibacterial agents include, but are not limited to, amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristan, demeclocycline, dicloxacillin, dirithromycin, doxycycline, erythromycin, enafloxacin, ertepenem, ethambutol, flucloxacillin, fosfomycin, furazolidone, gatifloxacin, geldanamycin, gentamicin, herbimicin, imipenem, isoniazide, kanamicin, levofloxacin, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, ofloxacin, oxytetracycline, penicillin, piperacillin, platensimycin, polymixin B, prontocil, pyrazinamide, quinupristine, rifampin, retapamulin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, alkylating agents include, but are not limited to, chlorambucil, chlormethine, cyclophosphamide, ifosfamide, melphalan, carmustine, fotemustine, lomustine, streptozocin, carboplatin, cisplatin, oxaliplatin, BBR3464, busulfan, dacarbazine, procarbazine, temozolomide, thioTEPA, and uramustine.

In certain embodiments, anti-metabolite agents include, but are not limited to, aminopterin, methotrexate, pemetrexed, raltitrexed, cladribine, clofarabine, fludarabine, mercaptopurine, pentostatin, tioguanine, cytarabine, fluorouracil, floxuridine, tegafur, carmofur, capecitabine and gemcitabine.

In certain embodiments, mitotic inhibitors include, but are not limited to, docetaxel, paclitaxel, vinblastine, vincristine, vindesine, and vinorelbine.

In certain embodiments, tyrosine kinase inhibitors include, but are not limited to, dasatinib, erlotinib, gefitinib, imatinib, lapatinib, nilotinib, sorafenib, and sunitinib.

In certain embodiments, topoisomerase inhibitors include, but are not limited to, etoposide, etoposide phosphate, teniposide, camptothecin, topotecan, and irinotecan.

In certain embodiments, cancer immunotherapy monoclonal antibodies include, but are not limited to, rituximab, alemtuzumab, bevacizumab, cetuximab, gemtuzumab, panitumumab, tositumomab, and trastuzumab.

In certain embodiments, anti-tumor antibiotic agents include, but are not limited to, anthracycline, mithramycin, fludarabine, gemcetobine, daunorubicin, doxorubicin, epirubicin, idarubicin, mitoxantrone, valrubicin, actinomycin, bleomycin, mitomycin, plicamycin, and hydroxyurea.

In certain embodiments, anti-cancer agents include, but are not limited to, amsacrine, asparaginase, altretamine, hydroxycarbamide, lonidamine, pentostatin, miltefosine, masoprocol, estramustine, tretinoin, mitoguazone, topotecan, tiazofurine, irinotecan, alitretinoin, mitotane, pegaspargase, bexarotene, arsenic trioxide, imatinib, denileukin diftitox, bortezomib, celecoxib, and anagrelide.

In certain embodiments, autophagy-inducing agents include, but are not limited to, rapamycin, concanavalin A, eEF-2 kinase inhibitors, and SAHA.

In certain embodiments, anti-psoriasis drugs include, but are not limited to, AEB071, AIN457, U0267, BIRT 2584, SRT2104, ILV-095, PH-10, tetrathiomolybdate, ASP015K, VB-201, RWJ-445380, botulinum toxin, CF101, CNTO 1275, CTA018, ILV-094, LY2439821, BT061, AMG 827, PTH (1-34), QRX-101, CNTO 1959, CTLA4Ig, AMG 139, and MK-0873.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

In various embodiments, the present invention provides a method of treating a proliferative or inflammatory disease in a patient in need thereof comprising administering a therapeutically effective amount of one or more compounds of the Formula I:

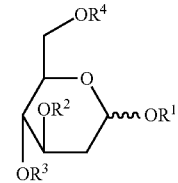

or a salt, ester or prodrug thereof, wherein each $R^1$, $R^2$, $R^3$ and $R^4$ are independently H, or $COR^5$; wherein each $R^5$ is independently selected from the group $C_1$-$C_{10}$ straight- or branched-chain alkyl, $C_4$-$C_{10}$ alkylcycloalkyl, and $C_3$-$C_{10}$ cycloalkyl.

In certain embodiments, $R^2$ and $R^3$ are $COR^5$. In certain embodiments, $R_5$ is independently selected from the group $C_3$-$C_7$ straight- or branched-chain alkyl, $C_4$-$C_{10}$ alkylcycloalkyl, and $C_3$-$C_7$ cycloalkyl. In particular, embodiments, the compounds are selected from those illustrated in Table 1.

In various embodiments, the proliferative disease is cancer. In certain embodiments, the cancer is brain, lung, breast, colorectal, prostate, gastric, esophageal, colon, pancreatic, ovarian, and/or hematologic cancer. In particular embodiments, the cancer is glioblastoma, high-grade glioma, and metastatic brain cancer.

Without being bound by theory, it is envisioned that the compounds presented herein may exert the effects by eliciting autophagy in addition to, or in lieu of apoptosis. Autophagy is a regulated process in which portions of the cytoplasm are first sequestered with double-membrane vesicles known as autophagosomes. Klionsky, D. J., et al., *Autophagy as a Regulated Pathway of Cellular Degradation*, Science, 2000, 290:1717-1721. These autophagosomes then fuse with lysosomes to become autolysosomes or degradative autophagic vacuoles, after which the sequestered contents are degraded by lysosomal hydrolases. Autophagy leads to the extensive degradation of organelles, including mitochondria, which precedes nuclear destruction.

Autophagy is induced in various cell conditions; for example, it is responsible for the degradation of normal proteins in response to nutrient deprivation, differentiation, aging, transformation, and cancer. Cuervo, A. M., *Autophagy: In Sickness and in Health*, Trends Cell Biol, 2004, 14: 70-77; Shintani, T., et al., *Autophagy in Health and Disease: A Double-Edged Sword*, Science, 2004, 306: 990-995. In cancer research, autophagy is a novel concept, and its role remains unclear. In general, cancer cells show less autophagic degradation than normal cells. Bursch, W., et al., *Programmed Cell Death (PCD). Apoptosis, Autophagic PCD, or Others?* Ann. N.Y. Acad. Sci., 2000, 926: 1-12; Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906. Indeed, Beclin1, a mammalian homologue of yeast autophagy-related gene Atg6, plays a role of a tumor suppressor. Liang, X. H., et al., *Induction of Autophagy and Inhibition of Tumorigenesis by Beclin 1*, Nature, 1999, 402: 672-676; Qu, X., et al., *Promotion of Tumorigenesis by Heterozygous Disruption of the Beclin 1 Autophagy Gene*, J Clin Invest, 2003, 112:1809-1820; Yue. Z., et al., *Beclin 1, an Autophagy Gene Essential. For Early Embryonic Development, Is a Haploinsufficient Tumor Suppressor*, Proc Natl Acad Sci USA, 2003, 100: 15077-15082.

In contrast, numerous cancer treatments have been shown to induce autophagy in established cancer cell lines. Altan, N., et al., *Defective Acidification in Human Breast Tumor Cells and Implications for Chemotherapy*, J Exp Med, 1998, 187: 1583-1598; Paglin, S., et al., *A Novel Response of Cancer Cells to Radiation Involves Autophagy and Formation of Acidic Vesicles*, Cancer Res, 2001, 61: 439-444; Kanzawa, T., et al., *Induction of Autophagic Cell Death in Malignant Glioma Cells by Arsenic Trioxide*, Cancer Res, 2003, 63: 2103-2108; Daido, S., et al., *Inhibition of the DNA-Dependent Protein Kinase Catalytic Subunit Radiosensitizes Malignant Glioma Cells by Inducing Autophagy*, Cancer Res, 2005, 65:4368-4375; Takeuchi, H., et al., *Synergistic Augmentation of Rapamycin-Induced Autophagy in Malignant Glioma Cells by Phosphatidylinositol 3-Kinase/Protein Kinase B Inhibitors*, Cancer Res, 2005, 65:3336-3346. However, whether autophagy helps kill tumor cells or instead protects them from the treatments' cell-damaging effect is still debated. Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906; Edinger, A. L., et al. *Defective Autophagy Leads to Cancer*, Cancer Cell, 2003, 4:422-424; Kondo, Y., et al., *Role of Autophagy in Cancer Development and Response to Therapy*, Nat Rev Cancer, 2005, 5:726-734; Halt, W. N., et al., *A Matter of Life or Death (or Both): Understanding Autophagy in Cancer*, Clin Cancer Res., 2006 Apr. 1, 12(7 Pt 1):1961-5.

Currently, methods to detect or quantify autophagy are somewhat limited. Demonstration of autophagic vacuoles on electron microscopy is an important standard; however, this analysis requires considerable skill and is neither easy nor quick. Other assays such as acridine orange or monodansyl cadaverine staining are not specific to autophagy. Paglin, S., et al., *A Novel Response of Cancer Cells to Radiation Involves Autophagy and Formation of Acidic Vesicles*, Cancer Res, 2001, 61: 439-444; Munafo, D. B., et al., *A Novel Assay to Study Autophagy: Regulation of Autophagosome Vacuole Size by Amino Acid Deprivation*, J Cell Sci, 2001, 114:3619-29. The use of the green-fluorescent protein (GFP)-tagged-rat microtubule-associated protein 1 light chain 3 (LC3) expression vector makes autophagy detection specific and easy, but this assay requires gene transfection and is not available for xenograft models or surgical specimens obtained from cancer patients. Kabeya, Y., et al., *LC3, a Mammalian Homologue of Yeast Apg8p, Is Localized in Autophagosome Membranes After Processing*, EMBO J, 2000, 19:5720-5728; Mizushima, N., et al., *Dissection of Autophagosome Formation Using Apg5-Deficient Mouse Embryonic Stem Cells*, J Cell Biol, 2001, 152:657-668.

The compounds presented herein are useful to treat a neurodegenerative disease, such as Alzheimer's disease, or Parkinson's disease.

Furthermore, the compounds and methods that are described herein can be used to prevent or treat Central Nervous System ("CNS") diseases and conditions such as CNS inflammatory and conditions, e.g., multiple sclerosis and progressive multifocal leukoencephalopathy.

Moreover, the compounds and methods that are described herein can be used to prevent or treat inflammatory diseases and conditions, such as osteoarthritis, Rheumatoid arthritis, Crohn's disease, ulcerative colitis, and auto-immune diseases such as lupus and mixed auto-immune disease.

Diseases and conditions such as telangectasia, venous angiomas, hemangioblastoma, and polycythemia vera may also be advantageously prevented or treated with the compounds and methods described herein.

These compounds and methods can affect stem cell survival and differentiation by maintaining stem cell stemness, e.g., preventing the differentiation of stem cells.

The compounds taught herein may also be used for the augmentation of immune response, particularly where the augmentation of the immune response leads to the expression of costimulatory molecules on the peripheral macrophages and tumor-infiltrating microglia. These compounds are also useful when the immune response leads to proliferation of effector T cells and/or up-regulation of several key intracellular signaling molecules that critically regulate T-cell and monocyte activation. The compounds are useful when the immune responses leads to up-regulation of several key intracellular signaling molecules that critically regulate T-cell and monocyte activation, particularly phosphorylation of Syk (Tyr(352)) in monocytes and ZAP-70 (Tyr (319)) in T cells.

The compounds presented herein to treat cancer may be administered in combination with one or more compounds and/or other agents including but not limited to anti-cancer agents, anti-angiogenic agents and/or autophagy inducing agents.

Anti-Cancer Agents

Anti-cancer agents that are suitable for use in the methods described herein include: antitumor antibiotics (anthracyclines, mitoxantrone, bleomycin, mithramycin); Fludarabine, Gemcitabine, temozolomide (Temodar); cyclophosphamides; fluoropyrimidines (such as capecitabine); fluorouracil (5-FU or Adrucil); nitrosoureas, such as procarbazine (Matulane), lomustine, CCNU (CeeBU), 3-[(4-amino-2-methyl-pyrimidin-5-yl)methyl]-1-(2-chloroethyl)-1-nitroso-urea carmustine (ACNU), (BCNU, BiCNU, Gliadel Wafer), and estramustine (Emcyt); nitrogen mustard; melphalan; chlorambucil; busulfan; ifosfamide nitrosoureas; thiotepa; antimitotic agents such as *vinca* alkaloids (e.g., vincristine) and taxoids (e.g., Taxol (paclitaxel)), Taxotere (docetaxel), epothilone analogs, discodermolide analogs, and eleutherobin analogs (e.g., ifosfamide, melphalan, chlorambucil, thiotepa, cisplatin, and carboplatin).

Temodar and other suitable anti-cancer agents may be administered at therapeutically effective dosages under different schedules, as envisioned by people of ordinary skill in the art. For instance, the anti-cancer agents can be administered at 100 mg per $m^2$ body weight for seven consecutive days on a bi-weekly basis. The anti-cancer agents may also be administered at the same dosage for 21 days on and 7 days off. Other therapeutic dosages and administration schedules can also be envisioned by people of ordinary skill in the art.

Anti-Angiogenic Agents

The anti-angiogenic agents useful in the disclosed methods include VEGF inhibitors (e.g., Avastin), VEGF Trap, Sorafenib, Sutent, linomide inhibitors of integrin-$\alpha\beta3$ function, angiostatin, razoxane, and the like.

Such anti-angiogenic agents may be small molecules, anti-bodies, aptamers, proteins, polypeptides, and other compounds or compositions that reduce or eliminate angiogenic activity. Anti-angiogenic agents may be administered at a therapeutically effective dose under different schedules. As an example, Avastin may be administered to a patient at a dose of 5, 10 or 15 mg per kg body weight once every two or three weeks. Alternatively, 3-20 mg/kg once every 2-3 weeks is suitable.

Autophagy-Inducing Agents

One or more autophagy-inducing agents may also be used in the methods presented herein. For instance, Rapamycin is useful as an autophagy-inducing agent. Other autophagy-inducing agents include concanavalin A, inhibitors of eEF-2 Kinase Inhibitors and histone deactylase inhibitors like SAHA.

The basis for adding one or more autophagy inducing agents to the combination therapies of the present invention is that our results indicate that sugar-based inhibitors of glycolysis kill tumor cells through this process. Autophagy is a regulated process in which portions of the cytoplasm are first sequestered with double-membrane vesicles known as autophagosomes. Klionsky, D. J., et al., *Autophagy as a Regulated Pathway of Cellular Degradation*, Science, 2000, 290:1717-1721. These autophagosomes then fuse with lysosomes to become autolysosomes or degradative autophagic vacuoles, after which the sequestered contents are degraded by lysosomal hydrolases. Autophagy leads to the extensive degradation of organelles, including mitochondria, which precedes nuclear destruction.

Autophagy is induced in various cell conditions; for example, it is responsible for the degradation of normal proteins in response to nutrient deprivation, differentiation, aging, transformation, and cancer. Cuervo, A. M., *Autophagy: In Sickness and in Health*, Trends Cell Biol, 2004, 14: 70-77; Shintani, T., et al., *Autophagy in Health and Disease: A Double-Edged Sword*, Science, 2004, 306: 990-995. In cancer research, autophagy is a novel concept, and its role remains unclear. In general, cancer cells show less autophagic degradation than normal cells. Bursch, W., et al., *Programmed Cell Death (PCD). Apoptosis, Autophagic PCD, or Others?* Ann. N.Y. Acad. Sci., 2000, 926: 1-12; Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906. Indeed, Beclin1, a mammalian homologue of yeast autophagy-related gene Atg6, plays a role of a tumor suppressor. Liang, X. H., et al., *Induction of Autophagy and Inhibition of Tumorigenesis by Beclin 1*, Nature, 1999, 402: 672-676; Qu, X., et al., *Promotion of Tumorigenesis by Heterozygous Disruption of the Beclin 1 Autophagy Gene*, J Clin Invest, 2003, 112:1809-1820; Yue. Z., et al., *Beclin 1, an Autophagy Gene Essential For Early Embryonic Development, Is a Haploinsufficient Tumor Suppressor*, Proc Natl Acad Sci USA, 2003, 100: 15077-15082.

The combination therapies of the present invention are particularly suitable for treating brain tumors including primary tumors such as glioblastoma or high-grade gliomas, and secondary brain tumors such as metastatic brain tumors. One unique property of the CNS is its striking predilection to uptake glucose and its analogs.

Hypoglycemic Agents

It is further envisioned that more optimal results will be obtained with the combination therapies if the patient is also treated with a therapeutically effective amount of one or more hypoglycemic agents under different schedules, preferably before treatment with compounds described herein. Hypoglycemic agents suitable for the present invention include compounds that reduce blood glucose levels. Non-limiting examples of such compounds include insulin, alpha-glucosidase inhibitors, sulfonylureas, meglitinides, D-phenylalanine derivatives, biguanides, thiazolidinediones, GLP-1 analogues, DPP-4 Inhibitors, and the like.

Thus, in another aspect, certain embodiments provide methods for treating proliferative or inflammatory disease in a human or animal subject in need of such treatment comprising administering to said subject an amount of a compound disclosed herein effective to reduce or prevent said disease in the subject, in combination with at least one additional agent for the treatment of said disease that is known in the art. In a related aspect, certain embodiments provide therapeutic compositions comprising at least one compound disclosed herein in combination with one or more additional agents for the treatment of inflammatory proliferative or inflammatory diseases.

Specific diseases to be treated by the compounds, compositions, and methods disclosed herein include, but are not limited to, proliferative or inflammatory diseases, psoriasis, plaque psoriasis, psoriasis vulgaris, localized pustular psoriasis, pustule psoriasis, Hallopeau localized continuous achrodermatitis, pustular palm psoriasis, pustular sole psoriasis, generalized pustular psoriasis, von Zumbuch generalized pustular psoriasis, milia psoriasis, Hallopeau generalized continuous dermatitis, herpetiform impetigodermatitis, atopic dermatitis, seborrheic dermatitis, contact dermatitis, numular dermatitis, generalized exfoliative dermatitis, statis dermatitis, perioral dermatitis, acne, rosacea, boils, carbuncles, pemphigus, cellulitis, Grover's disease, hidradenitis suppurativa, lichen planus, chronic lichen simplex, rhinophyma, pseudofolliculitis barbae, inflammatory reactions, drug eruptions, erythema, erythema multiforme, erythema nodosum, granuloma annulare, eczema, xerosis, terosis, ichthyosis, epidermolytic hyperkeratosis, keratoses, pruritis, cradle cap, scales, fresh stretch marks, dermatoses, burns, skin hypersensitivity reactions (including poison ivy and poison oak), decubitus ulcers, pressure ulcers, diabetic ulcers, epidermolysis bullosa, eczematoid dermatitis, pemphigus, bullous pemphigoid, epidermolysis bullosa, urticaria, angioedema, vasculitides, dermal eosinophilia, vitiligo, alopecia areata, skin cancers, cutaneous T cell lymphoma, basal cell carcinoma, nodular basal cell carcinoma, cystic basal cell carcinoma, cicatricial basal cell carcinoma, infiltrative basal cell carcinoma, Micronodular basal cell carcinoma, superficial basal cell carcinoma, pigmented basal cell carcinoma, Jacobi ulcer, fibroepithelioma of Pinkus, polypoid basal cell carcinoma, pore-like basal cell carcinoma, aberrant basal cell carcinoma, squamous cell carcinoma, adenoid squamous cell carcinoma, clear cell squamous cell carcinoma, spindle cell squamous cell carcinoma, signet-ring cell squamous cell carcinoma, basaloid squamous cell carcinoma, verrucous carcinoma, keratoacanthoma, Bowen's disease, Marjolin's ulcer, melanoma, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, dermatofibrosarcoma protuberans, Merkel cell carcinoma, Kaposi's sarcoma, spindle cell tumors, sebaceous carcinomas, microcystic adnexal carcinoma, Pagets's disease, atypical fibroxanthoma, leimyosarcoma, angiosarcoma, and Merkel cell carcinoma.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Methods

General Synthetic Methods for Preparing Compounds

The compounds disclosed herein can be synthesized according to the procedures described in WO 2010005799 (paragraphs [0086]-[0145]); WO 2009108926 (paragraphs [0173]-[0185]); WO 2008131024 (paragraphs [0067]-[0072]); US 20100152121 (paragraphs [0067]-[0083]); U.S. Pat. No. 7,160,865 (columns 11-13); and U.S. Pat. No. 6,979,675 (columns 28-29), the disclosures of which are hereby incorporated by reference as if written herein in their entireties.

Examples

The invention is further illustrated by the following examples.

Synthesis of 1-O-acyl-2-deoxy-D-glucopyranose

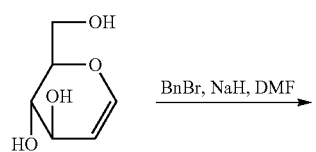

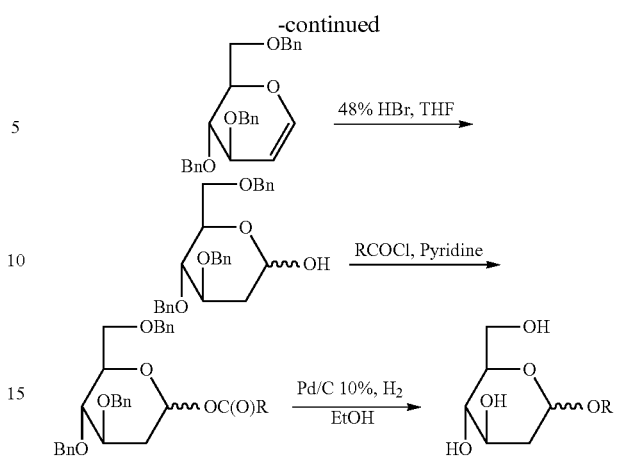

3,4,6-Tri-O-Benzyl-2-Deoxy-D-Glucopyranose

Solution of 2-deoxy-D-glucopyranose (1.46 g, 10 mmol) in DMF (15 mL) was prepared and cooled down to −10° C. Sodium hydride (60% suspension in mineral oil) (1.99 g, 50 mmol) was added and the mixture was stirred for 30 min. Benzyl bromide (6.85 g, 40 mmol) was added, the cooling bath was removed and the reaction mixture was stirred at room temperature until all substrate was converted into product. The mixture was cooled down to 0° C., and water (50 ml) was added slowly, followed by DCM (50 mL). Organic layer was separated, washed with water until neutral, then with brine, and dried over anhydrous sodium sulfate. Drying agent and solvents were removed and product was purified by low pressure column chromatography (LPC), using hexanes:ethyl acetate gradient (0 to 20% of EtOAc) for elution.

Fractions contained product were pooled together, evaporated to dryness and dried under reduced pressure to give 3.03 g of product. Yield 73%, $^1$H NMR (CDCl$_3$, δ), ppm: 7.34-7.24 (m, 15H, H arom.), 6.43 (dd, 1H, J=6.1 Hz, J=1.1 Hz, H-1), 4.88 (dd, 1H, J=6.1 Hz, J=2.7 Hz, H-2), 4.84 (d, 1H, J=11.4 Hz, CH$_2$Ph), 4.67-4.54 (m, 5H, CH$_2$Ph), 4.22 (m, 1H, H-3), 4.07 (ddd, 1H, J=8.2 Hz, J=4.7 Hz, J=3.2 Hz, H-5), 3.87 (dd, 1H, J=6.2 Hz, J=8.6 Hz, H-4), 3.81 (dd, 1H, J=4.9 Hz, J=10.9 Hz, H-6), 3.76 (dd, 1H, J=3.1 Hz, J=10.9 Hz, H-6').

3,4,6-Tri-O-Benzyl-2-Deoxy-D-Glucopyranose

48% Hydrobromic acid (0.5 mL, 4.5 mmol) was added to a solution of 3,4,6-tri-O-benzyl-D-glucal (2.08 g, 5 mmol) in THF (50 mL), and obtained mixture was stirred at room temperature for 20 min., (TLC control). After reaction was completed water (20 mL) followed by sodium carbonate (2.25 mmol, 239 mg) were added and the mixture was stirred for additional 10 min. The reaction mixture was extracted with ethyl acetate (3×30 mL). Combined organic extracts were washed with water until neutral and dried over sodium sulfate. Drying agent and solvents were removed and product was purified by crystallization (ethyl acetate/hexanes) Yield 76%, α:β ratio=3:1

$^1$H NMR (CDCl$_3$, δ), ppm: 7.38-7.14 (m, 30H, H arom. α, β), 5.40 (m, 1H, H-1α), 4.89 (d, 1H, J=10.9 Hz, CH$_2$Ph α), 4.88 (d, 1H, J=10.9 Hz, CH$_2$Ph β), 4.77 (m, 1H, H-1β), 4.70-4.50 (m, 9H, CH$_2$Ph α, CH$_2$Ph β), 4.08-4.00 (m, 2H, H-3a, H-5α), 3.75-3.60 (m, 5H, H-6α, H-6β, H-6'α, H-6'β), 3.50 (m, 3H, H-4α, H-4β, H-5β), 3.26 (d, 1H, J=6.3 Hz, OH β), 2.66 (m, 1H, OH α), 2.37 (ddd, 1H, J=12.5, Hz, J=5.1 Hz, J=2.2 Hz, H-2eβ), 2.29 (dd, 1H, J=12.9 Hz, J=5.0 Hz, H-2eα), 1.69 (dd, 1H, J=J=12.4 Hz, H-2aα), 1.57 (ddd, 1H, J=J=12.1 Hz, J=9.7 Hz, H-2β).

1-O-Acyl-3,4,6-Tri-O-Benzyl-2-Deoxy-D-Glucopyranose—General Procedure

Solution of 3,4,6-tri-O-benzyl-2-deoxy-D-glucopyranose (4.34 g, 10 mmol) and pyridine (1.62 mL, 20 mmol) in DCM (30 mL) was prepared and cooled down to 0° C. Acyl chloride (11 mmol) was slowly added and the mixture was stirred in room temperature overnight. DCM (50 mL), was added and the reaction mixture was washed with water (2×30 mL), brine (40 mL) then dried over sodium sulfate. Drying agent and solvents were removed and product was purified by LPC using hexanes:ethyl acetate gradient (0 to 20% of AcOEt) for elution. Fractions contained product were pooled together, evaporated to dryness and dried under reduced pressure. Following compounds were prepared according to this procedure:

3,4,6-Tri-O-Benzyl-1-O-Butyryl-2-Deoxy-D-Glucopyranose

Yield 92%, α: β ratio=2:1
$^1$H NMR (CDCl$_3$, δ) ppm: 7.38-7.19 (m, 30H, Harom. α,β), 6.31 (m, 1H, H-1α), 5.73 (dd, 1H, J=10.0 Hz, J=2.1 Hz, H-1β), 4.93 (d, 1H, J=10.7 Hz, CH$_2$Ph), 4.91 (d, 1H, J=10.7 Hz, CH$_2$Ph), 4.73-4.51 (m, 10H, CH$_2$Ph α β), 3.97 (ddd, 1H, J=11.5 Hz, J=8.6 Hz, J=5.0 Hz, H-3α), 3.87 (ddd, 1H, J=10.0 Hz, J=3.6 Hz, J=2.2 Hz, H-5α), 3.83-3.63 (m, 7H, H-6α, H-6β, H-6'α, H-6'β, H-4α, H-4β, H-3β), 3.55 (ddd, 1H, J=9.2 Hz, J=3.5 Hz, J=2.3 Hz, H-5β), 2.43-2.27 (m, 6H, H-2eα, H-2eβ, CH$_2$COα, CH$_2$COβ), 1.87 (ddd, 1H, J=13.6 Hz, J=11.4 Hz, J=3.4, H-2α) 1.80-1.58 (m, 5H, CH$_2$α, CH$_{43}$, H-2aβ), 0.98 (t, 3H, J=7.6 Hz, CH$_3$β), 0.95 (t, 3H, J=7.6 Hz, CH$_3$β).

3,4,6-Tri-O-Benzyl-1-O-(2-Ethyl)Butyryl-2-Deoxy-β-D-Glucopyranose

Yield 79%
$^1$H NMR (CDCl$_3$, δ) ppm: 7.38-7.17 (m, 15H, Harom.), 5.74 (dd, 1H, J=10.0 Hz, J=2.2 Hz, H-1), 4.91 (d, 1H, J=10.8 Hz, CH$_2$Ph), 4.72 (d, 1H, J=11.6 Hz, CH$_2$Ph), 4.65-4.51 (m, 4H, CH$_2$Ph), 3.82-3.70 (m, 3H, H-3, H□6□□H□6), 3.65 (dd, 1H, J=9.6 Hz, J=9.4 Hz, H-4), 3.54 (ddd, 1H, J=9.4 Hz, J=J=2.6 Hz, H-5), 2.39 (ddd, 1H, J=12.3 Hz, J=4.8 Hz, J=2.1 Hz, H-2e), 2.34-2.23 (m, 1H, CHCO), 1.84-1.45 (m, 5H, H-2a, 2CH$_2$), 1.00-0.85 (M, 6H, 2CH$_3$)

3,4,6-Tri-O-Benzyl-1-O-Valproyl-2-Deoxy-β-D-Glucopyranose

Yield 73%
$^1$H NMR (CDCl$_3$, δ) ppm: 7.38-7.17 (m, 15H, Harom.), 5.73 (dd, 1H, J=10.0 Hz, J=2.1 Hz, H-1), 4.89 (d, 1H, J=10.9 Hz, CH$_2$Ph), 4.70 (d, 1H, J=11.6 Hz, CH$_2$Ph), 4.65-4.51 (m, 4H, CH$_2$Ph), 3.79-3.67 (m, 3H, H-3, H□6□□H□6□), 3.63 (dd, 1H, J=8.6 Hz, J=9.3 Hz, H-4), 3.51 (ddd, 1H, J=9.3 Hz, J=3.3 Hz, J=2.6 Hz, H-5), 2.46-2.30 (m, 2H, H-2e, CHCO), 1.81-1.21 (m, 9H, H-2a, CH$_2$) 0.90 (t, 3H, J=7.2 Hz, CH$_3$)

1-O-Acyl-2-Deoxy-D-Glucopyranose—General Procedure

Pd/C Degussa type (10% (50% wet)) (0.4 g) was added to the solution of 1-O-acyl-3,4,6-tri-O-benzyl-2-deoxy-D-glucopyranose (5 mmol) in ethanol (50 mL). Obtained mixture was hydrogenated at room temperature using Paar apparatus with hydrogen (45 psi). After reaction was completed (TLC control), catalyst was filtered off and the solvent was evaporated to dryness to give a crude product. Product was purified by LPC using chloroform:methanol gradient (0-10% of MeOH) for elution. Fractions contained product were pooled together, evaporated to dryness and dried under reduced pressure.

Following compounds were prepared according to this procedure:

1-O-Butyryl-2-Deoxy-D-Glucopyranose (WP1212)

Yield 82%, α:β ratio=3.4:1, $[α]^D$+74°, (c=1.26, methanol)
$^1$H NMR (DMSO-d6, δ) ppm: 6.07 (d, 1H, J=2.1 Hz, H-1α), 5.63 (dd, 1H, J=10.1 Hz, J=2.1 Hz, H-1β), 5.00 (d, 1H, J=5.4 Hz, OHα), 4.96 (d, 1H, J=4.9 Hz, OHβ), 4.93 (d, 1H, J=5.1 Hz, OHβ), 4.89 (d, 1H, J=4.9 Hz, OHα), 4.52 (dd, 1H, J=J=6.1 Hz, OHβ), 4.48 (dd, 1H, J=5.6 Hz, J=6.1 Hz, OHα), 3.70-3.38 (m, 8H, H-3α, H-3β, H-5α, H-5β, H-6α, H-6β), 3.14 (ddd, 1H, J=J=9.2 Hz, J=5.3 Hz, H-4α), 3.03 (ddd, 1H, J=J=9.2 Hz, J=5.0 Hz, H-4β), 2.01 (dd, 2H, J=J=7.5 Hz, CH$_2$COα, CH$_2$COβ), 2.01 (ddd, 1H, J=12.3 Hz, J=5.0 Hz, J=2.1 Hz, H-2eβ), 1.93 (ddd, 1H, J=12.7 Hz, J=5.0 Hz, J=1.4 Hz, H-2eα), 1.63-1.50 (m, 5H, CH$_2$α, CH$_2$β, H-2aα), 1.45 (ddd, 1H, J=13.6 Hz, J=J=11.7 Hz, H-2aβ), 1.11 (dd, 1H, J=7.1 Hz, J=4.0 Hz, CH$_2$β) 1.03 (t, 3H, J=7.5 Hz, CH$_3$α), 1.02 (t, 3H, J=7.5 Hz, CH$_3$α)

1-O-Valproyl-2-Deoxy-β-D-Glucopyranose (WP1490)

Yield 76%,
$^1$H NMR (DMSO-d6, δ) ppm: 5.60 (d, 1H, J=9.9 Hz, H-1), 3.63 (d, 1H, J=11.8 Hz, H-6), 3.53-3.42 (m, 2H, H-3, H-6), 3.17-3.12 (m, 1H, H-5), 3.02 (dd, 1H, J=9.0 Hz, J=9.2 Hz, H-4), 2.35-2.27 (m, 1H, CHCO), 1.99 (ddd, 1H, J=12.0, J=4.6 Hz, J=2.1 Hz, H-2e), 1.57-1.32 (m, 5H, H-2a, 2CH$_2$), 1.28-1.18 (m, 4H, 2CH$_2$), 0.83 (t, 6H, 2CH$_3$)

1-O-(2-Ethyl)Butyryl-2-Deoxy-β-D-Glucopyranose (WP1474)

Yield %,
$^1$H NMR (DMSO-d6+D$_2$O, δ) ppm: 5.64 (d, 1H, J=9.9 Hz, H-1), 3.64 (d, 1H, J=11.8 Hz, H-6), 3.51-3.39 (m, 2H, H-3, H-6), 3.15 (ddd, 1H, J=9.4 Hz, J=5.3 Hz, J=1.7 Hz, H-5), 3.03 (dd, 1H, J=9.2 Hz, J=8.9 Hz, H-4), 2.23-2.15 (m, 1H, CHCO), 2.00 (ddd, 1H, J=12.0, J=4.7 Hz, J=1.7 Hz, H-2e), 1.56-1.44 (m, 5H, H-2a, 2CH$_2$), 0.84 (t, 3H, J=7.2 Hz, CH$_3$), 0.83 (t, 3H, J=7.4 Hz, CH$_3$)

Synthesis of 3-O-Valproyl-2-Deoxy-D-Glucopyranose

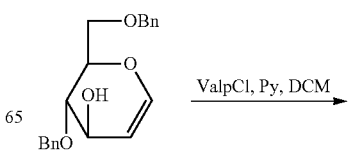

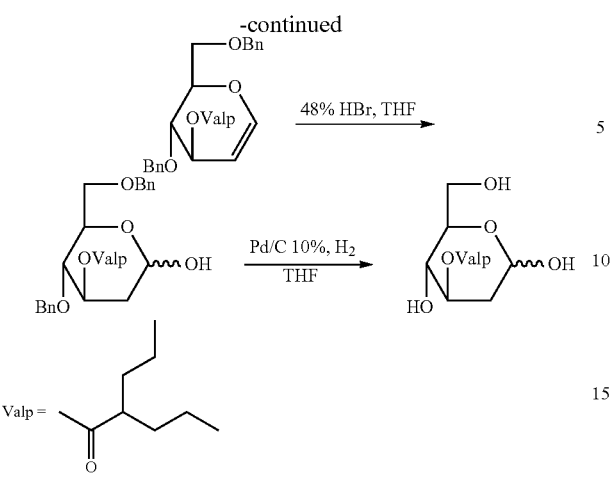

Synthesis of 4,6-Di-Benzyl-3-O-Valproyl-2-Deoxy-D-Glucopyranose 4,6-di-O-benzyl-2-deoxy-D-glucopyranose (2.0 g, 6.1 mmol) was dissolved in DCM (20 mL). Pyridine (14 mmol, 1.2 mL) followed by valproyl chloride (9.2 mmol, 1.6 mL) was added and obtained mixture was stirred at room temperature. After reaction was completed (TLC control), the mixture was diluted with DCM (100 mL) and washed with water (2×40 mL), then with brine, and dried over anhydrous $Na_2SO_4$. Drying agent and solvent were removed and product was purified by LPC using hexanes:ethyl acetate gradient (0-10% of AcOEt) for elution. Fractions contained product were pooled together and evaporated to dryness to give 2.76 g (6.1 mmol, yield 100%) of pure product.

$^1$H NMR (CDCl$_3$, 500 MHz, δ) ppm: 7.38-7.22 (m, 10H, Harom.), 6.44 (d, 1H, J=6.0 Hz, H-1), 5.43 (m, 1H, H-3), 4.78 (dd, 1H, J=6.0 Hz, J=2.9 Hz, H-2), 4.74 (d, 1H, J=11.3 Hz, CH$_2$-Ph), 4.62 (d, 1H, J=11.3 Hz, CH$_2$Ph), 4.61 (d, 1H, J=12.2 Hz, CH$_2$Ph), 4.56 (d, 1H, J=12.2 Hz, CH$_2$Ph), 4.11 (ddd, 1H, J=8.0 Hz, J=4.6 Hz, J=2.7 Hz, H-5), 3.93 (dd, 1H, J=8.4 Hz, J=8.0 Hz, H-4), 3.82 (dd, 1H, J=10.8 Hz, J=4.6 Hz, H-6), 3.73 (dd, 1H, J=10.8 Hz, J=2.7 Hz, H-6'), 2.35 (h, 1H, J=6.1 Hz, CHCO), 1.65-1.55 (m, 2H, CH$_2$), 1.46-1.36 (m, 2H, CH$_2$), 1.34-1.24 (m, 4H, CH$_2$), 0.87 (t, 3H, J=9.0 Hz, CH$_3$), 0.85 (t, 3H, J=8.3 Hz, CH$_3$)

Synthesis of 4,6-Di-Benzyl-3-O-Valproyl-2-Deoxy-α-D-Glucopyranose 4,6-Di-benzyl-3-O-valproyl-2-deoxy-D-glucopyranose (2.76 g, 6.1 mmol) was dissolved in THF (30 mL). 48% HBr (water solution) (0.5 mL, 4.5 mmol) was added and the reaction mixture was stirred at room temperature. After reaction was completed (TLC control), the reaction mixture was diluted with water (15 mL). The mixture was neutralized by addition of solid Na$_2$CO$_3$ (2.25 mmol, 238.5 mg) and water (30 mL). THF was evaporated and residue was dissolved in ethyl acetate (100 mL). Organic solution was washed with water, then with brine, and dried over anhydrous Na$_2$SO$_4$. Drying agent and solvent was removed under reduced pressure and product was purified by LPC using hexanes:ethyl acetate gradient (0-20% of AcOEt) for elution. Fractions contained product were pooled together and evaporated to dryness to give 1.8 g (3.8 mmol) (yield 62.8%) of 4,6-di-benzyl-3-O-valproyl-2-deoxy-D-glucopyranose $^1$H NMR (CDCl$_3$, 500 MHz, δ) ppm: 7.38-7.12 (m, 10H, Harom.), 5.39 (bs, 1H, H-1), 5.37 (ddd, 1H, J=12.1 Hz, J=9.0 Hz, J=5.0 Hz, H-3), 4.73 (d, 1H, J=11.1 Hz, CH$_2$Ph), 4.61 (d, 1H, J=12.2 Hz, CH$_2$Ph), 4.51 (d, 1H, J=12.2 Hz, CH$_2$Ph), 4.49 (d, 1H, J=11.1 Hz, CH$_2$Ph), 4.10 (ddd, 1H, J=9.8 Hz, J=4.2 Hz, J=2.1 Hz, H-5), 3.72 (dd, 1H, J=10.6 Hz, J=4.3 Hz, H-6), 3.65 (dd, 1H, J=10.6 Hz, J=2.0 Hz, H-6'), 3.64 (dd, 1H, J=J=9.8 Hz, H-4), 2.74 (bs, 1H, OH), 2.41-2.28 (m, 2H, H-2a, CHCO), 1.71 (ddd, 1H, J=11.0 Hz, J=3.6 Hz, J=2.0 Hz, H-2e), 1.64-1.18 (m, 8H, CH$_2$), 0.85 (t, 3H, J=7.2 Hz, CH$_3$), 0.82 (t, 3H, J=7.2 Hz, CH$_3$)

3-O-Valproyl-2-Deoxy-D-Glucopyranose (WP1512)

Pd/C Degussa type (10% (50% wet)) (0.145 g) was added to the solution of 4,6-di-O-benzyl-3-O-valproyl-D-glucopyranose (0.6 g) in THF (12 mL). Obtained mixture was hydrogenated at room temperature using Paar apparatus with hydrogen (48 psi). After reaction was completed (TLC control), catalyst was filtered off and the solvent was evaporated to dryness. Product was purified by LPC using gradient CHCl$_3$:MeOH (0 to 10% of MeOH) as eluent. Fractions contained product were pooled together, evaporated to dryness and dried under reduced pressure, to give pure product.

Yield %, α:β ratio=2:1

$^1$H NMR (DMSO-d6, δ) ppm: 5.14 (bs, 1H, H-1α), 5.01 (ddd, 1H, J=J=10.5 Hz, J=5.0 Hz, H-3α), 4.69 (m, 2H, J=9.3 Hz, H-1β, H-3β), 3.67-3.61 (m, 1H, H-5α), 3.60 (d, 1H, J=11.8 Hz, H-6α), 3.55-3.45 (m, 3H, H-6'α, H-6β, H-6'β), 3.28 (dd, 1H, J=9.6 Hz, J=9.5 Hz, H-4α), 3.21 (dd, 1H, J=9.5 Hz, J=9.1 Hz, H-4β), 3.17-3.12 (m, 1H, H-5β), 2.32-2.24 (m, 2H, CHCOα, CHCOβ), 2.00 (dd, 1H, J=11.4 Hz, J=4.4 Hz, H-2eβ), 1.88 (dd, 1H, J=12.4 Hz, J=5.0 Hz, H-2eα), 1.52 (m, 18H, H-2aα, H-2aβ, 4CH$_2$α, 4CH$_2$β), 0.82 (t□□12H, J=7.2 Hz, 2CH$_3$a, 2CH$_3$β)

Synthesis of 3-O-(2-Ethyl)Butyryl-2-Deoxy-D-Glucopyranose

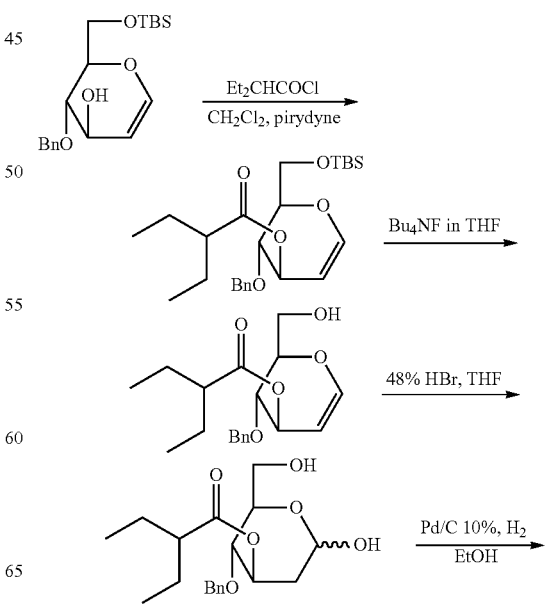

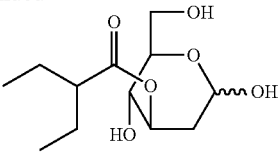

Synthesis of 4-O-Benzyl-3-O-(2-Ethyl)Butyryl-6-O-Tert-Butyldimethylsilyl-2-Deoxy-D-Glucopyranose 3-O-benzyl-6-O-tert-butyldimethylsilyl-2-deoxy-D-glucopyranose (3 mmol) and pyridine (6 mmol) were dissolved in dichloromethane (20 mL). The reaction mixture was cooled down to 0° C. (2-ethyl)butyryl chloride (4.5 mmol) was added. The reaction mixture was stirred at room temperature for 1 hr, then it was diluted with DCM (50 mL), washed with water (3×50 mL), and dried over anhydrous sodium sulfate. Drying agent was filtered off, solvent was evaporated to dryness and product was separated by LPC using hexanes:ethyl acetate gradient (0-5% of AcOEt) as eluent. Fractions contained product were combined and evaporated to give pure 4-O-benzyl-3-O-(2-ethyl)butyryl-6-O-tert-butyldimethylsilyl-2-deoxy-D-glucopyranose.

Yield 77%, $[\alpha]^D$ −0.22 (c=1.0, chloroform)

$^1$H NMR (CDCl$_3$, 300 MHz, δ) ppm: 7.35-7.27 (m, 5H, Haromat.), 6.41 (d, 1H, J=6.0 Hz, H-1), 5.45-5.41 (m, 1H, H-3), 4.75 (dd, 1H, J=6 Hz, J=3 Hz, H-2), 4.76 (d, 1H, J=11.2 Hz, CH$_2$Ph), 4.75 (dd, 1H, J=6 Hz, J=3 Hz, H-2), 4.70 (d, 1H, J=11.2 Hz, CH$_2$Ph), 3.98-3.93 (m, 2H, H-6, H-6'), 3.92-3.84 (m, 2H, H-4, H-5), 2.24-2.17 (m, 1H, CHCO), 1.70-1.48 (m, 4H, 2CH$_2$), 0.91 (s, 9H, tBu), 0.92-0.87 (m, 6H, 2CH$_3$), 0.08 (s, 6H, Me$_2$)

Synthesis of 4-O-Benzyl-3-O-(2-Ethyl)Butyryl-2-Deoxy-D-Glucopyranose

Solution of 4-O-benzyl-3-O-(2-ethyl)butyryl-6-O-tert-butyldimethylsilyl-2-deoxy-D-glucopyranose (3.9 mmol) in THF (30 mL) was prepared and cooled down to 0° C.

Tetrabutylammonium fluoride (4.3 mmol) was added and the reaction mixture was stirred at room temp. After reaction was completed, the reaction mixture was diluted with water (60 mL) and extracted with ethyl acetate (3×30 mL). Combined extracts were washed with water and dried over anhydrous sodium sulfate. Drying agent and solvent were removed and product was purified by LPC using hexanes:ethyl acetate gradient (0-10% of AcOEt) as eluents. Fractions contained product were pooled together to give pure 4-O-benzyl-3-O-(2-ethyl)butyryl-2-deoxy-D-glucopyranose (3.75 mmol, yield 96%).

$^1$H NMR (CDCl$_3$, 300 MHz, δ) ppm: 7.38-7.27 (m, 5H, Harom.), 6.41 (dd, 1H, J=6 Hz, J=1.3 Hz, H-1), 5.48 (ddd, 1H, J=6.4 Hz, J=2.5 Hz, J=1.3 Hz, H-3), 4.80 (dd, 1H, J=6.1 Hz, J=2.6 Hz, H-2), 4.79 (d, 1H, J=11.3 Hz, CH$_2$Ph), 4.68 (d, 1H, J=11.3 Hz, CH$_2$Ph), 4.01-3.84 (m, 4H, H-4, H-5, H-6), 2.27-2.17 (m, 1H, CHCO), 1.73-1.46 (m, 4H, CH$_2$), 0.90 (t, 3H, J=7.4 Hz, CH$_3$), 0.90 (t, 3H, J=7.5 Hz, CH$_3$)

Synthesis of 4-O-Benzyl-3-O-(2-Ethyl)Butyryl-2-Deoxy-D-Glucopyranose

4-O-benzyl-3-O-(2-ethyl)butyryl-2-deoxy-D-glucopyranose (4.3 mmol) was dissolved in THF (45 mL). 48% Water solution of HBr (1 mL, 9 mmol) was added and the reaction mixture was stirred at room temperature. After 30 min., reaction was completed, and water (45 mL) was added. The mixture was neutralized by addition of solid Na$_2$CO$_3$ (4.5 mmol, 477 mg). Obtained solution was extracted with ethyl acetate (3×40 mL). Combined organic extracts were washed with water, brine and dried over anhydrous sodium sulfate. Solids and solvents were removed and crude product was purified by LPC using hexanes:ethyl acetate gradient (0-20% of AcOEt) for elution. Fractions contained product were pooled together and evaporated to dryness to give pure 4-O-benzyl 3-O-(2-ethyl)butyryl-2-deoxy-D-glucose (3.48 mmol, yield 81%), α:β ratio=1.9:1

$^1$H NMR (DMSO-d6+D$_3$O, 300 MHz, δ) ppm: 7.34-7.25 (m, 5H, Harom.), 5.20 (ddd, 1H, J=11.4 Hz, J=9.5 Hz, J=5 Hz, H-3α), 5.18 (d, 1H, J=3 Hz, H-1α), 4.95 (ddd, 1H, J=11.7 Hz, J=9.2 Hz, J=5.2 Hz, H-3β), 4.78 (dd, 1H, J=10 Hz, J=2.2 Hz, H-1β), 4.63 (s, 2H, CH$_2$Ph α), 4.61 (s, 2H, CH$_2$Ph β), 3.76 (ddd, 1H, J=9.7 Hz, J=J=3.0 Hz, H-3α), 3.68-3.54 (m, 5H, H-5α, H-6α, H-6'α, H-6β, H-6'β), 3.54 (dd, 1H, J=9.4 Hz, H-4α), 3.35-3.33 (m, 1H, H-5β), 2.20-1.98 (m, 4H, CHCOα, CHCOβ, H-2eα, H-2eβ), 1.58-1.34 (m, 6H, H-2aα, H-2aβ, CH$_2$α, CH$_2$β), 0.83-0.75 (m, 6H, CH$_3$α, CH$_3$β)

Synthesis of 3-O-(2-Ethyl)Butyryl-2-Deoxy-D-Glucopyranose (WP1342)

Pd/C Degussa type (10%, contained 50% of water) (60 mg) was added to the solution of 4-O-benzyl-3-O-(2-ethyl)butyryl-2-deoxy-D-glucopyranose (1.7 mmol) in ethyl alcohol (70 mL). The mixture was hydrogenated using Paar apparatus with hydrogen (50 psi) for 24 hr. The reaction mixture was then filtered through Celite, evaporated to dryness, and product was purified by LPC using chloroform:methanol gradient (0-20% of MeOH) for elution. Fractions contained product were pooled together and evaporated to dryness to give pure 3-O-(2-ethyl)butyryl-2-deoxy-D-glucose (1.24 mmol, yield 73%), α:β ratio=1.5:1

$^1$H NMR (DMSO-d6+D$_2$O, 300 MHz, δ) ppm: 5.14 (d, 1H, J=2.3 Hz, H-1α), 5.03 (ddd, 1H, J=11.5 Hz, J=9.4 Hz, J=9.4 Hz, J=5.1 Hz, H-3α), 4.73 (ddd, 1H, J=11.9 Hz, J=8.6 Hz, J=5.2 Hz, H-3β), 4.69 (dd, 1H, J=10.2 Hz, J=1.5 Hz, H-1β), 3.65 (dd, 1H, J=10.7 Hz, J=1.9 Hz, H-6α), 3.63 (dd, 1H, J=10.0 Hz, J=2.3 Hz, H-6β), 3.50 (dd, 1H, J=11.7 Jz, J=5.0 Hz, H-6'α), 3.45-3.02 (m, 2H, H-5α, H-6'β), 3.28 (dd, 1H, J=J=9.5 Hz, H-4α), 3.18 (dd, 1H, J=J=8.7 Hz, H-4β), 3.17-3.11 (m, 1H, H-5β), 2.19-2.06 (m, 2H, CHCOα, CHCOβ), 2.00 (ddd, 1H, J=12.0 Hz, J=5.2 Hz, J=1.7 Hz, H-2eβ), 1.90 (dd, 1H, J=12.2 Hz, J=4.6 Hz, H-2eα), 1.58-1.38 (m, 5H, CH$_2$α, CH$_2$β), 1.32 (ddd, 1H, J=11.9 Hz, J=J=11.8 Hz, H-2aβ), 0.82 (t, 3H, J=7.3 Hz, CH$_3$α), 0.90 (t, 3H, J=7.5 Hz, CH$_3$β)

Synthesis of 4-O-Valproyl-2-Deoxy-D-Glucopyranose (WP1513)

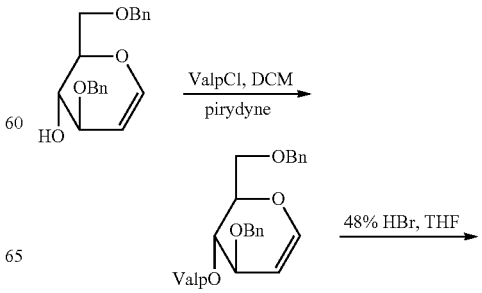

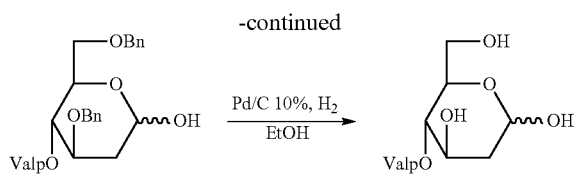

Synthesis of 3,6-Di-O-Benzyl-4-O-Valproyl-2-Deoxy-D-Glucopyranose 3,6-di-O-benzyl-2-deoxy-D-glucopyranose (3.4 g, 10.4 mmol) was dissolved in DCM (15 mL). Pyridine (24.7 mmol, 2.0 mL) followed by valproyl chloride (12 mmol, 1.9 mL) were added and obtained mixture was stirred at room temperature. After reaction was completed (TLC control), the mixture was diluted with DCM (100 mL) and washed with water (2×40 mL), then with brine, and dried over anhydrous $Na_2SO_4$. Drying agent and solvent were removed and product was purified by LPC using hexanes:ethyl acetate gradient (0-10% of AcOEt) for elution. Fractions contained product were pooled together and evaporated to dryness to give 3.71 g (8.2 mmol) of pure product. Yield (85.3%)

$^1$H NMR (CDCl$_3$, 300 MHz, δ) ppm: 7.34-7.26 (m, 5H, H arom.), 6.48 (dd, 1H, J=6.3 Hz, J=0.8 Hz, H-1), 5.30 (dd, 1H, J=J=4.5 Hz, H-4), 4.89 (dd, 1H, J=6.3 Hz, J=4.0 Hz, H-2), 4.60 (s, 2H, CH$_2$Ph), 4.58 (d, 1H, J=12.0 Hz, CH$_2$Ph), 4.50 (d, 1H, J=12.0 Hz, CH$_2$Ph), 4.36-4.29 (m, 1H, H-5), 3.92 (dd, 1H, J=J=4.0 Hz, H-3), 3.78 (dd, 1H, J=10.6 Hz, J=7.4 Hz, H-6), 3.66 (dd, 1H, J=10.6 Hz, J=4.0 Hz, H-6), 2.45-2.32 (m, 1H, CHCO), 1.70-1.17 (m, 8H, 4CH$_2$), 0.87 (t, 3H, J=7.2 Hz, CH$_3$), 0.85 (t, 3H, J=7.2 Hz, CH$_3$)

Synthesis of 3,6-Di-O-Benzyl-4-O-Valproyl-2-Deoxy-α-D-Glucopyranose 3,6-di-benzyl-4-O-valproyl-2-deoxy-D-glucopyranose (3 g, 6.6 mmol) was dissolved in THF (30 mL). 48% HBr (water solution) (2 mL, 18 mmol) was added and the reaction mixture was stirred at room temperature. After reaction was completed (TLC control), the reaction mixture was diluted with water (15 mL). The mixture was neutralized by addition of solid Na$_2$CO$_3$ (9 mmol, 954 mg). THF was evaporated and ethyl acetate (100 mL) was added to the residue. Organic solution was washed with water, then with brine, and dried over anhydrousNa$_2$SO$_4$. Drying agent and solvent were removed and product was purified by LPC using hexanes:ethyl acetate gradient (0-20% of AcOEt) for elution. Fractions contained product were pooled together and evaporated to dryness to give pure 3,6-di-O-benzyl-4-O-valproyl-2-deoxy-α-D-glucopyranose 1.8 g (3.8 mmol) (yield 58%).

$^1$H NMR (CDCl$_3$, 300 MHz, δ) ppm: 7.34-7.26 (m, 5H, H arom.), 5.42 (bs, 1H, H-1), 4.93 (dd, 1H, J=9.8 Hz, J=9.3 Hz, H-4), 4.59 (d, 2H, J=12.1 Hz, CH$_2$Ph), 4.50 (d, 1H, J=12.1 Hz, CH$_2$Ph), 4.48 (d, 1H, J=12.1 Hz, CH$_2$Ph), 4.16 (ddd. 1H, J=9.8 Hz, J=5.8 Hz, J=3.5 Hz, H-5), 4.00 (ddd, 1H, J=11.2 Hz, J=9.1 Hz, J=4.9 Hz, H-3), 3.56-3.45 (m, 2H, H-6, H-6'), 3.0 (bs, 1H, OH), 2.37-2.22 (m, 2H, H-2e, CHCO), 1.80-1.11 (m, 9H, H-2a, 4CH$_2$), 0.80 (t, 3H, J=7.2 Hz, CH$_3$), 0.77 (t, 3H, J=7.2 Hz, CH$_3$)

4-O-Valproyl-2-Deoxy-D-Glucopyranose (WP1513)

Pd/C Degussa type (10% (50% wet)) (0.290 g) was added to the solution of 3,6-di-O-benzyl-4-O-valproyl-2-deoxy-D-glucopyranose (1.5 g) in EtOH (20 mL). Obtained mixture was hydrogenated at room temperature using Paar apparatus with hydrogen (50 psi). After 12 hr. reaction was completed, catalyst was filtered off and the solvent was evaporated to give a crude product. Product was purified by LPC using CHCl$_3$:MeOH gradient (0-10% of MeOH) for elution. Fractions contained product were pooled together, evaporated to dryness and dried under reduced pressure, to give pure 4-O-valproyl-2-deoxy-D-glucopyranose (0.64 g, yield 69%), α:β ratio=2:1

$^1$H NMR (DMSO-d6, δ) ppm: 5.14 (d, 1H, J=2.2 Hz, H-1α), 4.65 (d, 1H, J=7.9 Hz, H-1β), 4.53 (dd, 1H, J=J=9.6 Hz, H-4α), 4.44 (dd, 1H, J=J=9.8 Hz, H-4β), 3.76 (ddd, 1H, J=12.1 Hz, J=9.6 Hz, J=5.0 Hz, H-3α), 3.70 (ddd, 1H, J=9.8 Hz, J=5.7 Hz, J=2.2 Hz, H-5α), 3.55 (ddd, 1H, J=11.8 Hz, J=9.2 Hz, J=5.1 Hz, H-3β), 3.47-3.20 (m, 5H, H-6α, H-6'α, H-6β, H-6'β, H-53), 2.37-2.24 (m, 2H, CHCOα, CHCOβ), 1.98 (dd, 1H, J=11.0 Hz, J=5.1 Hz, H-2eβ), 1.86 (dd, 1H, J=12.1 Hz, J=5.2 Hz, H-2eα), 1.58-1.15 (m, 18H, H-2aα, H-2aβ, 4CH$_2$α, 4CH$_2$β), 0.84 (t, 6H, J=7.0 Hz, CH$_3$), 0.83 (t, 6H, J=7.9 Hz, CH$_3$)

Synthesis of 6-O-Acyl-2-Deoxy-D-Glucopyranose

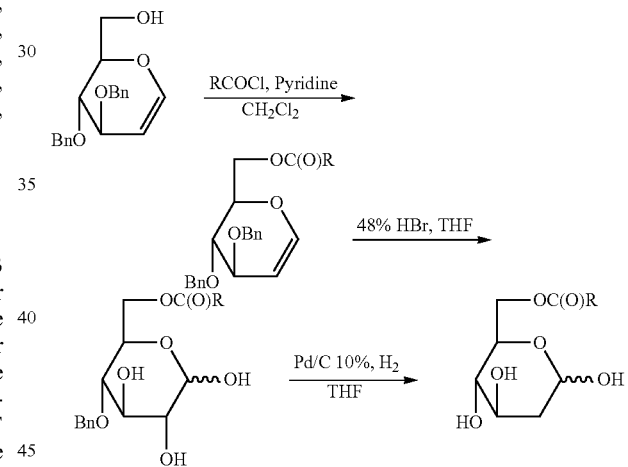

Synthesis of 6-O-Acyl-3,4-Di-O-Benzyl-2-Deoxy-D-Glucopyranose 3,4-di-O-benzyl-2-deoxy-D-glucopyranose (2.76 mmol) and pyridine (5.52 mmol), were dissolved in dichloromethane (20 mL). Obtained solution was cooled down to 0° C., and acyl chloride (3 mmol) was added. The mixture was stirred at 0° C. After reaction was completed (TLC control), the reaction mixture was diluted with dichloromethane (30 mL), washed with water (3×50 mL), and dried over anhydrous sodium sulfate. Drying agent and solvent were removed and product was purified by LPC using hexanes:ethyl acetate gradient (0-10% of AcOEt) for elution. Fractions contained product were pooled together and evaporated to dryness to give pure product. Following compounds were obtained according to this procedure:

3,4-Di-O-Benzyl-6-O-(2-Ethyl)Butyric-2-Deoxy-D-Glucopyranose

Yield 80%

$^1$H NMR (CDCl$_3$, 300 MHz, δ) ppm: 7.37-7.22 (m, 10H, Harom.), 6.38 (dd, 1H, J=6.2 Hz, J=1.2 Hz, H-1), 4.90 (dd, 1H, J=6.2 Hz, J=2.7 Hz, H-2), 4.86 (d, 1H, J=11.4 Hz, CH$_2$Ph), 4.66 (d, 2H, J=11.9 Hz, CH$_2$Ph), 4.56 (d, 1H, J=11.4 Hz, CH$_2$Ph), 4.50 (dd, 1H, J=12.1 Hz, J=2.7 Hz, H-6), 4.36 (dd, 1H, J=12.1 Hz, J=5.4 Hz, H-6'), 4.22 (ddd, 1H, J=6 Hz, J=2.6 Hz, J=1.3 Hz, H-3), 4.10 (ddd, 1H, J=8.2 Hz, J=5.4 Hz, J=2.6 Hz, H-5), 3.79 (dd, 1H, J=8.5 Hz, J=6 Hz, H-4), 2.30-2.20 (m, 1H, CHCO), 1.72-1.45 (m, 4H, 2CH$_2$), 0.89 (t, 6H, J=7.4 Hz, 2CH$_3$)

3,4-Di-O-Benzyl-6-O-Valproyl-2-Deoxy-D-Glucopyranose

Yield 76%

$^1$H NMR (CDCl$_3$, 300 MHz, δ) ppm: 7.38-7.27 (m, 10H, Harom.), 6.38 (dd, 1H, J=6.2 Hz, J=1.2 Hz, H-1), 4.90 (dd, 1H, J=6.2 Hz, J=2.7 Hz, H-2), 4.86 (d, 1H, J=11.4 Hz, CH$_2$Ph), 4.66 (d, 2H, J=11.9 Hz, CH$_2$Ph), 4.56 (d, 1H, J=11.4 Hz, CH$_2$Ph), 4.50 (dd, 1H, J=12.1 Hz, J=2.7 Hz, H-6), 4.36 (dd, 1H, J=12.1 Hz, J=5.4 Hz, H-6'), 4.22 (ddd, 1H, J=6 Hz, J=2.6 Hz, J=1.3 Hz, H-3), 4.10 (ddd, 1H, J=8.2 Hz, J=5.4 Hz, J=2.6 Hz, H-5), 3.79 (dd, 1H, J=8.5 Hz, J=6 Hz, H-4), 2.30-2.20 (m, 1H, CHCO), 1.72-1.45 (m, 8H, 4CH$_2$), 0.89 (t, 6H, J=7.4 Hz, 2CH$_3$)

Synthesis of 6-O-Acylo-3,4-Di-O-Benzyl-2-Deoxy-D-Glucopyranose

6-O-acylo-3,4-di-O-benzyl-2-deoxy-D-glucopyranose (1.1 mmol) was dissolved in THF (10 mL). 48% Water solution of HBr (0.05 mL, 0.45 mmol) was added and the reaction mixture was stirred at room temperature. After reaction was completed (TLC control), the mixture was neutralized by dilution with water (10 mL) and addition of solid Na$_2$CO$_3$ (0.225 mmol, 24 mg). THF was evaporated and ethyl acetate (30 mL) was added to the residue. Organic solution was washed with water, then with brine, and dried over anhydrous. Na$_2$SO$_4$. Solids and solvents were removed and crude product was purified by LPC using hexanes:ethyl acetate gradient (0-20% of AcOEt) for elution. Fractions contained product were pooled together and evaporated to dryness to give pure product. Following compounds were obtained according with this procedure:

3,4-Di-O-Benzyl-6-O-(2-Ethyl)Butyric-2-Deoxy-D-Glucopyranose

Yield 80% α:β ratio=3:1

$^1$H NMR (CDCl$_3$, 300 MHz, δ) ppm: 7.40-7.28 (m, 10H, Harom.), 5.40 (bs, 1H, H-1α), 4.98 (d, 1H, J=10.8 Hz, CH$_2$Ph α), 4.97 (d, 2H, J=10.8 Hz, CH$_2$Ph β), 4.82 (m, 1H, H-1β), 4.74-4.60 (m, 6H, CH$_2$Phα, CH$_2$Phβ), 4.51 (dd, 1H, J=11.9 Hz, J=2.2 Hz, H-6α), 4.50 (dd, 1H, J=11.9 Hz, J=2.1 Hz, H-6β), 4.30 (dd, 1H, J=11.9 Hz, J=4.2 Hz, H-6'α), 4.28 (dd, 1H, J=11.9 Hz, J=4.2 Hz, H-6'β), 4.09 (m, 2H, H-3α, H-5α), 3.72 (ddd, 1H, J=11.2 Hz, J=7.9 Hz, J=4.9 Hz, H-3β), 3.57-3.53 (m, 1H, H-5β), 3.52 (dd, 1H, J=J=9.0 Hz, H-4α), 3.47 (dd, 1H, J=J=9.0 Hz, H-4β), 3.14 (1H, J=4.6 Hz, OHβ), 2.58 (bs, 1H OHα), 2.44 (ddd, 1H, J=12.9 Hz, J=4.9 Hz, J=1.3 Hz, H-2eβ), 2.34 (ddd, 1H, J=12.9 Hz, J=4.9 Hz, J=1.3 Hz, H-2eα), 2.33-2.23 (m, 2H, CHCoα, CHCOβ), 1.74-1.45 (m, 10H, H-2aα, H-2aβ, 2CH$_2$α, 2CH$_2$β), 0.92 (t, 12H, J=7.4 Hz, 2CH$_3$α, 2CH$_3$β)

3,4-Di-O-Benzyl-6-O-Valproylo-2-Deoxy-D-Glucopyranose

Yield 75%, α:β ratio=3:1

$^1$H NMR (CDCl$_3$, 300 MHz, δ) ppm: 7.40-7.28 (m, 10H, Harom.), 5.38 (bs, 1H, H-1α), 4.97 (d, 1H, J=10.8 Hz, CH$_2$Phα), 4.96 (d, 2H, J=10.8 Hz, CH$_2$Phβ), 4.81 (d, 1H, J=8.9 Hz, H-1β), 4.74-4.58 (m, 3H, CH$_2$Phα, CH$_2$Phβ), 4.50 (dd, 1H, J=12.1 Hz, J=1.9 Hz, H-6α), 4.48 (dd, 1H, J=11.9 Hz, J=2.1 Hz, H-6β), 4.30-4.20 (m, 2H, H-6'α, H-6'β), 4.09-4.00 (m, 2H, H-3α, H-5α), 3.70 (ddd, 1H, J=12.4 Hz, J=7.8 Hz, J=5.3 Hz, H-3β), 3.57-3.47 (m, 1H, H-5β), 3.49 (dd, 1H, J=J=9.3 Hz, H-4α), 3.46 (dd, 1H, J=J=9.0 Hz, H-4β), 2.53-2.36 (m, 3H, CHCOα, CHCOβ, H-2eβ), 2.32 (dd, 1H, J=13.0 Hz, J=5.0 Hz, H-2eα), 1.72-1.22 (m, 18H, H-2aα, H-2aβ, 4CH$_2$α, 4CH$_2$β), 0.89 (t, 12H, J=7.2 Hz, 2CH$_3$α, 2CH$_3$β)

Synthesis of 6-O-Acylo-2-Deoxy-D-Glucopyranose

Pd/C Degussa type (10%, contained 50% of water) (40 mg) was added to the solution of 6-O-acyl-3,4-di-O-benzyl-2-deoxy-D-glucopyranose (0.8 mmol) in ethyl alcohol (50 mL). The mixture was hydrogenated using Paar apparatus with hydrogen (35 psi) After reaction was completed (TLC control), the reaction mixture was filtered through Celite, and evaporated to dryness. Product was purified by LPC using chloroform:methanol gradient (0-10% of MeOH) for elution. Fractions contained product were pooled together and evaporated to dryness to give pure product. Following compounds were obtained according with this procedure:

6-O-(2-Ethyl)Butyric-2-Deoxy-D-Glucopyranose (WP1319)

Yield 98.5%

$^1$H NMR (DMSO-d6+D$_2$O, 300 MHz, δ) ppm: 5.10 (d, 1H, J=2.5 Hz, H-1α), 4.63 (dd, 1H, J=9.6 Hz, J=1.7 Hz, H-1β), 4.35 (dd, 1H, J=11.5 Hz, J=2.0 Hz, H-6α), 4.34 (dd, 1H, J=11.5 Hz, J=2.0 Hz, H-6β), 4.04 (dd, 1H, J=11.3 Hz, J=5.3 Hz, H-6'α), 4.01 (dd, 1H, J=11.3 Hz, J=5.3 Hz, H-6'β), 3.73 (ddd, 1H, J=9.6 HZ, J=5.3 Hz, J=2.0 Hz, H-5α), 3.67 (ddd, 1H, J=11.6 Hz, J=8.8 Hz, J=4.9 Hz, H-3α), 3.38 (ddd, 1H, J=12.1 Hz, J=8.6 HZ, J=5.0 Hz, H-3β), 3.26 (ddd, 1H, J=9.5 Hz, J=6.3 Hz, J=1.9 Hz, H-53), 3.04 (dd, 1H, J=J=9.3 Hz, H-4α), 2.95 (dd, 1H, J=J=9.2 Hz, H-43), 2.23-2.13 (m, 2H, CHCOα, CHCOβ), 1.92 (ddd, 1H, J=12.5 Hz, J=4.9 Hz, J=1.7 Hz, H-2eβ), 1.80 (d, 1H, J=12 Hz, J=5.0 Hz, H-2eα), 1.60-1.38 (m, 9H, 2CH$_2$α, 4CH$_2$β, H-2aα), 1.29 (ddd, 1H, J=10.0 Hz, J=J=12.1 Hz, H-2aβ), 0.84 (t, 12H, J=7.4 Hz, 2CH$_3$α, 2CH$_3$β)

6-O-Valproyl-2-Deoxy-D-Glucopyranose (WP1491)

Yield 80%, α:β ratio=2.5:1

$^1$H NMR (DMSO-d6+D$_2$O, 300 MHz, δ) ppm: 5.05 (d, 1H, J=2.5 Hz, H-1α), 4.60 (dd, 1H, J=9.7 Hz, J=1.7 Hz, H-1β), 4.33 (dd, 2H, J=11.6 Hz, J=1.8 Hz, H-6α, H-6β), 4.04-3.94 (m, 2H, H-6'α, H-6'β), 3.73-3.59 (m, 2H, H-3α, H-5α), 3.36 (ddd, 1H, J=11.5 Hz, J=8.5 Hz, J=5.0 Hz, H-3β), 3.22 (ddd, 1H, J=9.3 Hz, J=6.2 Hz, J=1.2 Hz, H-5β), 3.02 (dd, 1H, J=J=9.3 Hz, H-4α), 2.93 (dd, 1H, J=J=9.1 Hz, H-4β), 2.35-2.23 (m, 2H, CHCOα, CHCOβ), 1.90 (dd, 18H, J=10.7 Hz, J=5.0 Hz, H-20, H-2eα, 4CH$_2$α, 4CH$_2$β), 0.82 (t, 12H, J=7.2 Hz, 2CH$_3$α, 2CH$_3$β)

Synthesis of
1,3-Di-O-Acetyl-2-Deoxy-D-Glucopyranose

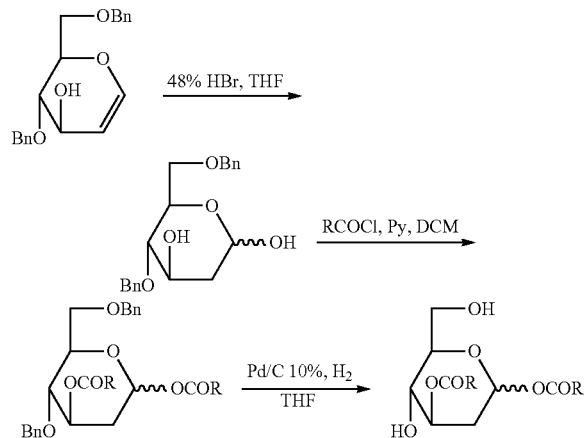

Synthesis of
4,6-Di-O-Benzyl-2-Deoxy-D-Glucopyranose 4,6-di-O-benzyl-2-deoxy-D-glucopyranose (4.9 mmol) was dissolved in THF (60 mL). 48% Water solution of HBr (0.4 mL, 3.6 mmol) was added and the reaction mixture was stirred at room temperature for 30 min.). After reaction was completed water (20 mL) followed by sodium carbonate (1.8 mmol, 191 mg) were added and the mixture was stirred for additional 10 min. The reaction mixture was extracted with ethyl acetate (3×40 mL). Combined organic extracts were washed with water until neutral and dried over sodium sulfate. Solids and solvents were removed and crude product was purified by LPC using hexanes:ethyl acetate gradient (0-20% of AcOEt) as eluents. Pure 4,6-di-O-benzyl-2-deoxy-D-glucose (3.1 mmol, yield 63%) was obtained.

Synthesis of 1,3-Di-O-Acyl-4,6-Di-O-Benzyl-2-Deoxy-D-Glucopyranose 4,6-Di-O-benzyl-2-deoxy-D-glucopyranose (3 mmol) was dissolved in dichloromethane (30 mL). Pyridine (18 mmol) was added, and the reaction mixture was cooled down to 0° C. Appropriate acyl chloride (9 mmol) was added, and the reaction mixture was stirred at room temperature until reaction was completed (TLC control), then reaction mixture was diluted with dichloromethane (70 mL), washed with water (3×50 mL) and dried over anhydrous sodium sulfate. Drying agent was filtered off, and solvent was evaporated. Toluene (50 mL) was added to the residue, and evaporated to dryness. Addition and evaporation of the toluene was repeated 3 times. Crude product was purified by LPC using hexanes:ethyl acetate gradient (0-10% of AcOEt) as eluents. Fractions contained product were pooled together and evaporated to dryness to give pure product. Following compounds were prepared according to this procedure 1,3-Di-O-(2-Ethyl)Butyryl-4,6-Di-O-Benzyl-2-Deoxy-β-D-Glucopyranose Yield 85%
$^1$H NMR (CDCl$_3$, 300 MHz, δ) ppm: 7.39-7.18 (m, 10H, Harom.), 5.82 (dd, 1H, J=10.0 Hz, J=2.2 Hz, H-1), 5.07 (ddd, 1H, J=11.3 Hz, J=9.1 Hz, J=5.3 Hz, H-3), 4.74 (d, 1H, J=11 Hz, CH$_2$Ph), 4.65 (d, 1H, J=12.2 Hz, CH$_2$Ph), 4.57 (d, 1H, J=11 Hz, CH$_2$Ph), 4.55 (d, 1H, J=12.2 Hz, CH$_2$Ph), 3.82-3.77 (m, 2H, H-4, H-6), 3.74 (dd, 1H, J=11.0 Hz, J=2.0 Hz, H-6'), 3.60 (ddd, 1H, J=9.5 Hz, J=3.2 Hz, J=2.1 Hz, H-5), 2.43 (ddd, 1H, J=12.3 Hz, J=5.3 Hz, J=2.3 Hz, H-2e), 2.31-2.18 (m, 2H, CHCO), 1.77 (ddd, 1H, J=12.3 Hz, J=J=10 Hz, H-2α), 1.70-1.48 (m, 8H, 4CH$_2$), 0.99-0.87 (m, 6H, 2CH$_3$)

1,3-Di-O-Valproyl-4,6-Di-O-Benzyl-2-Deoxy-β-D-Glucopyranose

Yield 80%
$^1$H NMR (CDCl$_3$, 300 MHz, δ) ppm: 7.35-7.14 (m, 10H, Harom.), 5.78 (dd, 1H, J=10.0 Hz, J=2.0 Hz, H-1), 5.04 (ddd, 1H, J=11.4 Hz, J=9.1 Hz, J=5.2 Hz, H-3), 4.72 (d, 1H, J=11 Hz, CH$_2$Ph), 4.63 (d, 1H, J=12.2 Hz, CH$_2$Ph), 4.56 (d, 1H, J=11 Hz, CH$_2$Ph), 4.55 (d, 1H, J=12.2 Hz, CH$_2$Ph), 3.78 (dd, 1H, J=J=11.5 Hz, H-4), 3.77 (dd, 1H, J=11.2 Hz, J=3.6 Hz, H-6), 3.71 (dd, 1H, J=11.2 Hz, J=1.9 Hz, H-6'), 3.58 (ddd, 1H, J=11.6 Hz, J=3.2 Hz, J=2.1 Hz, H-5), 2.45-2.30 (m, 3H, H-2e, 2CHCO), 1.80-1.51 (m, 5H, H-2a, 2CH$_2$), 1.50-1.20 (m, 12H, 6CH$_2$), 0.95-0.78 (m, 12H, 4CH$_3$)

Synthesis of
1,3-Di-O-Acyl-2-Deoxy-D-Glucopyranose

Pd/C Degussa type (10%, contained 50% of water) was added to the solution of 1,3-di-O-acyl-4,6-di-O-benzyl-2-deoxy-D-glucopyranose (1.7 mmol) in ethyl alcohol (150 mL). The mixture was hydrogenated using Paar apparatus with hydrogen (50 psi) for 24 hr. The reaction mixture was then filtered through Celite, evaporated to dryness, and product was purified by LPC using chloroform:methanol gradient (0-10% of MeOH) as eluent. Fractions contained product were pooled together and evaporated to dryness to give pure product. Following compounds were synthesized according to this procedure:

1,3-Di-O-(2-Ethyl)Butyryl-2-Deoxy-β-D-Glucopyranose (WP1261)

Yield 70%
$^1$H NMR (DMSO-d$_6$, 300 MHz, δ) ppm: 5.78 (dd, 1H, J=9.6 Hz, J=2.0 Hz, H-1), 5.18 (d, 1H, J=10.9 Hz, OH), 4.87 (ddd, 1H, J=11.6 Hz, J=8.4 Hz, J=5.4 Hz, H-3), 4.59 (dd, 1H, J=11.5 Hz, 6-OH), 3.67 (dd, 1H, J=10.7 Hz, J=5.6 Hz, H-6), 3.53 (ddd, 1H, J=10.7 Hz, J=J=4.7 Hz, H-6'), 3.42-3.35 (m, 2H, H-4, H-5), 2.24 (m, 3H, CHCO, H-2e), 1.61-1.39 (m, 9H, 4CH$_2$, H-2α), 0.87-0.80 (m, 6H, 2CH$_3$).

1,3-Di-O-Valproyl-2-Deoxy-β-D-Glucopyranose (WP1521)

Yield 70%
$^1$H NMR (CDCl$_3$, 300 MHz, δ) ppm: 5.81 (dd, 1H, J=9.9 Hz, J=1.2 Hz, H-1), 4.92 (ddd, 1H, J=10.6 Hz, J=9.1 Hz, J=5.4 Hz, H-3), 3.92 (dd, 1H, J=11.7 Hz, J=3.3 Hz, H-6), 3.83 (dd, 1H, J=11.7 Hz, J=4.3 Hz, H-6'), 3.68 (dd, 1H, J=J=9.3 Hz, H-3), 3.47 (ddd, 1H, J=9.5 Hz, J=4.0 Hz, J=3.3 Hz, H-5), 2.84 (bs, 1H, OH), 2.47-2.32 (m, 2H, 2CHCO), 2.28 (ddd, 1H, J=12.3 Hz, J=5.2 Hz, J=2.2 Hz, H-2e), 2.05 (bs, 1H, OH), 1.76 (dd, 1H, J=J=10.1 Hz, H-2α), 1.68-1.52 (m, 4H, 2CH$_2$), 1.50-1.21 (m, 12H, 6CH$_2$), 0.89 (t, 3H, J=7.2 Hz, CH$_3$), 0.88 (t, 3H, J=7.2 Hz, CH$_3$)

Synthesis of
1,6-Di-O-Acyl-2-Deoxy-D-Glucopyranose

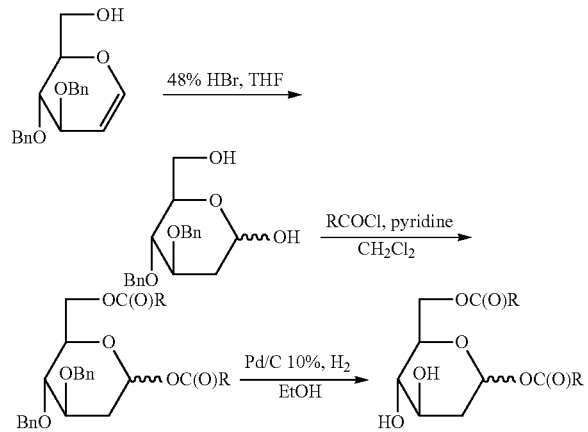

Synthesis of
3,4-Di-O-Benzyl-2-Deoxy-D-Glucopyranose

48% Hydrobromic acid (0.4 mL, 3.6 mmol) was added to the solution of 3,4-di-O-benzyl-2-deoxy-D-glucopyranose (3.5 mmol) in THF (25 mL). The reaction mixture was stirred at room temperature. After reaction was completed (TLC control), the reaction mixture was diluted with water (15 mL). The mixture was neutralized by addition of solid Na$_2$CO$_3$ (1.8 mmol, 191 mg). THF was evaporated and ethyl acetate (100 mL) was added to the residue. Organic solution was washed with water, then with brine, and dried over anhydrous Na$_2$SO$_4$. Drying agent and solvent were removed and product was separated by LPC using hexanes:ethyl acetate gradient (0-10% of AcOEt) for elution. Fractions contained product were pooled together and evaporated to dryness to give 3,4-di-O-benzyl-2-deoxy-D-glucopyranose (1.75 mmol, yield 50%).

$^1$H NMR (CDCl$_3$, 300 MHz, δ) ppm: 7.39-7.30 (m, 10H, Harom.), 5.38 (d, 1H, J=2.4 Hz, H-1α), 4.97 (d, 1H, J=11.0 Hz, CH$_2$Ph α), 4.96 (d, 1H, J=11.0 Hz, CH$_2$Ph β), 4.84 (d, 1H, J=8.4 Hz, H-1β), 4.74-4.62 (m, 3H, CH$_2$Phα, CH$_2$Phβ), 4.09 (ddd, 1H, J=11.3 Hz, J=8.8 Hz, J=4.9 Hz, H-3α), 3.95 (ddd, 1H, J=9.6 Hz, J=4.8 Hz, J=2.8 Hz, H-5α), 3.90-3.81 (m, 2H, H-6α, H-6β), 3.76-3.66 (m, 2H, H-6'α, H-6'β), 3.49 (dd, 1H, J=J=9.6 Hz, H-4α), 3.48 (dd, 1H, J=J=9.2 Hz, H-1β), 3.88 (ddd, 1H, J=9.3 Hz, J=4.8 Hz, J=2.6 Hz, H-53), 3.10 (bs, 1H, OH), 2.41 (ddd, 1H, J=12.6 Hz, J=5.0 Hz, J=1.9 Hz, H-2eβ), 2.32 (ddd, 1H, J=13.1 Hz, J=4.9 Hz, J=1.1 Hz, H-2eα), 1.67 (ddd, 1H, J=13.1 Hz, J=11.5 Hz, J=4.5 Hz, H-2aα), 1.58 (ddd, 1H, J=12.6 Hz, J=J=9.7 Hz, H-2aβ)

Synthesis of 1,6-Di-O-Acyl-3,4-Di-O-Benzyl-2-Deoxy-D-Glucopyranose—General Procedure The mixture of 3,4-di-O-benzyl-2-deoxy-D-glucopyranose (1.6 mmol) and pyridine (9.6 mmol) in dichloromethane (20 mL) was prepared and cooled down to 0° C. Acyl chloride (4.8 mmol) was added and the reaction mixture was stirred at room temperature. After reaction was completed, the reaction mixture was diluted with dichloromethane (80 mL) and washed with water (3×30 mL), then dried over anhydrous sodium sulfate. Drying agent and solvents were removed and product was separated by LPC with hexanes: ethyl acetate gradient (0-10% of AcOEt) for elution. Fractions contained product were pooled together and evaporated to dryness. Following compounds were obtained according to this procedure:

1,6-Di-O-Butyryl-3,4-Di-O-Benzyl-2-Deoxy-D-Glucopyranose

Yield 70%, α:β ratio=1.2:1
$^1$H NMR (CDCl$_3$, 300 MHz, δ) ppm: 7.38-7.28 (m, 10H, Harom.), 6.26 (d, 1H, J=1.9 Hz, H-1α), 5.723 (dd, 1H, J=10.0 Hz, J=2.3 Hz, H-1β), 4.97 (d, 1H, J=10.7 Hz, CH$_2$Ph α), 4.95 (d, 1H, J=10.7 Hz, CH$_2$Phβ), 4.74-4.60 (m, 3H, CH$_2$Phα, CH$_2$Phβ), 4.35-4.33 (m, 4H, H-6α, H-6'α H-6β, H-6'β), 4.00 (ddd, 1H, J=11.5 Hz, J=9.0 Hz, J=5.2 Hz, H-3α), 3.92 (ddd, 1H, J=10.0 Hz, J=J=3.5 Hz, H-5α), 3.78 (ddd, 1H, J=11.6 Hz, J=9.5 Hz, J=5.2 Hz, H-3β), 3.62 (ddd, 1H, J=9.6 Hz, J=J=3.7 Hz, H-53), 3.57 (dd, 1H, J=9.8 Hz, J=8.9 Hz, H-4α), 3.52 (dd, 1H, J=9.6 Hz, J=8.4 Hz, H-4β), 2.42-2.28 (m, 6H, H-2eα, H-2eβ, and CH$_2$CO), 1.84 (ddd, 1H, J=13.8 Hz, J=11.5 Hz, J=3.5 Hz, H-2aβ) 1.73-1.62 (m, 5H, H-2aα, and CH$_2$), 1.03-0.93 (m, 6H, CH$_3$)

1,6-Di-O-(2-Ethyl)Butyryl-3,4-Di-O-Benzyl-2-Deoxy-β-D-Glucopyranose

Yield 70%
$^1$H NMR (CDCl$_3$, 300 MHz, δ) ppm: 7.38-7.28 (m, 10H, Harom.), 5.73 (dd, 1H, J=9.9 Hz, J=2.2 Hz, H-1), 4.95 (d, 1H, J=10.8 Hz, CH$_2$Ph), 4.70 (d, 1H, J=10.8 Hz, CH$_2$Ph), 4.62 (d, 1H, J=10.8 Hz, CH$_2$Ph), 4.61 (d, 1H, J=10.8 Hz, CH$_2$Ph), 4.45 (dd, 1H, J=11.9 Hz, J=2.2 Hz, H-6), 4.25 (dd, 1H, J=11.9 Hz, J=5.0 Hz, H-6'), 3.76 (ddd, 1H, J=11.1 Hz, J=8.4 Hz, J=5.0 Hz, H-3), 3.60 (ddd, 1H, J=9.6 Hz, J=5.1 Hz, J=2.2 Hz, H-5), 3.50 (dd, 1H, J=9.6 Hz, J=8.5 Hz, H-4), 2.36 (ddd, 1H, J=12.4 Hz, J=4.8 Hz, J=2.1 Hz, H-2e), 2.29-2.17 (m, 2H, CHCO), 1.72 (ddd, 1H, J=11.6 Hz, J=J=10.2 Hz, H-2α) 1.66-1.43 (m, 8H, CH$_2$), 0.97-0.85 (m, 12H, CH$_3$)

1,6-Di-O-Valproyl-3,4-Di-O-Benzyl-2-Deoxy-β-D-Glucopyranose

Yield 70%
$^1$H NMR (CDCl$_3$, 500 MHz, δ) ppm: 7.36-7.27 (m, 10H, Harom.), 5.71 (dd, 1H, J=9.9 Hz, J=2.0 Hz, H-1), 4.94 (d, 1H, J=10.8 Hz, CH$_2$Ph), 4.70 (d, 1H, J=11.5 Hz, CH$_2$Ph), 4.68 (d, 1H, J=11.0 Hz, CH$_2$Ph), 4.64 (d, 1H, J=11.5 Hz, CH$_2$Ph), 4.47 (dd, 1H, J=11.9 Hz, J=1.9 Hz, H-6), 4.21 (dd, 1H, J=11.9 Hz, J=4.8 Hz, H-6'), 3.75 (ddd, 1H, J=11.5 Hz, J=8.5 Hz, J=4.9 Hz, H-3), 3.60 (ddd, 1H, J=9.5 Hz, J=4.6 Hz, J=1.9 Hz, H-5), 3.50 (dd, 1H, J=9.8 Hz, J=9.3 Hz, H-4), 2.45-2.32 (m, 3H, H-2e, 2CHCO), 1.75 (dd, 1H, J=J=11.6 Hz, H-2α), 1.66-1.56 (m, 4H, 2CH$_2$), 1.47-1.36 (m, 4H, 2CH$_2$), 1.35-1.24 (m, 8H, 4CH$_2$), 0.91-0.85 (m, 12H, 4CH$_3$)

Synthesis of 1,6-Di-O-Acyl-2-Deoxy-D-Glucopyranose—General Procedure

Pd/C Degussa type (10%, containing 50% of water) (100 mg) was added to the solution of 1,6-di-O-acyl-3,4-di-O- benzyl-2-deoxy-D-glucopyranose (1 mmol) in 95% anhydrous ethanol (100 mL). Obtained mixture was hydrogenated at room temperature using Paar apparatus with hydrogen (45 psi). After 24 hr. reaction was completed, catalyst was filtered off, and the solvent was evaporated to give a crude product. Product was purified by LPC, using chloroform:methanol gradient (0-10% of MeOH) as eluent.

Fractions contained product were pooled together, evaporated to dryness and dried under reduced pressure. Following compounds were prepared according to this procedure:

1,6-Di-O-Butyryl-2-Deoxy-D-Glucopyranose (WP1217)

Yield (94%), α:β ratio=1.28:1

$^1$H NMR (CDCl$_3$, 300 MHz, δ) ppm: 6.27 (d, 1H, J=2.2 Hz, H-1α), 5.78 (dd, 1H, J=10.2 Hz, J=2.3 Hz, H-1β), 4.72 (dd, 1H, J=12.5 Hz, J=3.1 Hz, H-6α), 4.71 (dd, 1H, J=12.5 Hz, J=3.4 Hz, H-6β), 4.18 (dd, 1H, J=12.5 Hz, J=2.2 Hz, H-6β), 4.18 (dd, 1H, J=12.5 Hz, J=2.2 Hz, H-6'α), 4.02 (ddd, 1H, J=11.6 Hz, J=9 Hz, J=5 Hz, H-3α), 3.82-3.74 (m, 2H, H-5α, H-3β), 3.48 (ddd, 1H, J=9.7 Hz, J=3.2 Hz, J=2.2 Hz, H-5β), 3.42 (bs, 1H, OH), 3.24 (dd, 1H, J=J=9.3 Hz, H-4α), 3.19 (dd, 1H, J=J=9.3 Hz, H-4β), 2.6 (bs, 1H, OH), 2.44-2.31 (m, 4H, CH$_2$), 2.25 (ddd, 1H, J=12.4 Hz, J=5.0 Hz, J=2.2 Hz, H-2eβ), 2.19 (ddd, 1H, J=13.7 Hz, J=5.0 Hz, J=1.4 Hz, H-2e a), 1.81 (ddd, 1H, J=13.7 Hz, J=11.8 Hz, J=3.6 Hz, H-2aα), 1.72 (ddd, 1H, J=J=12.0 Hz, J=10.2 Hz, H-2β), 1.69-1.63 (m, 4H, CH$_2$), 0.98 (t, 3H, J=7.4 Hz, CH$_3$), 0.97 (t, 3H, J=7.3 Hz, CH$_3$)

1,6-Di-O-(2-Ethyl)Butyryl-2-Deoxy-D-Glucopyranose (WP1262)

Yield (78%), α:β ratio=1.1:1

$^1$H NMR (CDCl$_3$, 300 MHz, δ) ppm: 6.29 (d, 1H, J=2.6 Hz, H-1α), 5.78 (dd, 1H, J=10.1 Hz, J=2.2 Hz, H-1β), 4.69 (dd, 1H, J=12.4 Hz, J=3.4 Hz, H-6α), 4.61 (dd, 1H, J=12.3 Hz, J=3.8 Hz, H-6α), 4.24 (dd, 1H, J=12.3 Hz, J=2.3 Hz, H-6'β), 4.12 (dd, 1H, J=12.4 Hz, J=2.2 Hz, H-6'α), 4.01 ppm (ddd, 1H, J=11.5 Hz, J=8.9 Hz, J=5.0 Hz, H-3α), 3.80-3.71 (m, 2H, H-3β, H-5α), 3.49 (bs, 1H, OH), 3.47 (ddd, 1H, J=11.7 Hz, J=3.8 Hz, J=2.4 Hz, H-5β), 3.38 (bs, 1H, OH), 3.23 (dd, 1H, J=J=9.5 Hz, H-4α), 3.20 (dd, 1H, J=J=9.1 Hz, H-4β), 2.69 (bs, 2H, OH), 2.35-2.20 (m, 3H, H-20, CHCO), 2.17 (ddd, 1H, J=13.4 Hz, J=5.1 Hz, J=1.3 Hz, H-2eα), 1.81 (ddd, 1H, J=13.6 Hz, J=11.7 Hz, J=3.6 Hz, H-2aα), 1.73-1.50 (m, 9H, CH$_2$ and H-2aβ), 0.94-0.87 (m, 12H, CH$_3$)

1,6-Di-O-Valproyl-2-Deoxy-D-Glucopyranose (WP1489)

Yield (78%), α:β ratio=1:4

$^1$H NMR (CDCl$_3$, 300 MHz, δ) ppm: 6.27 (d, 1H, J=2.7 Hz, H-1α), 5.75 (dd, 1H, J=10.0 Hz, J=2.0 Hz, H-1β), 4.71 (dd, 1H, J=12.5 Hz, J=2.9 Hz, H-6α), 4.60 (dd, 1H, J=12.4 Hz, J=3.4 Hz, H-6β), 4.21 (dd, 1H, J=12.4 Hz, J=2.2 Hz, H-6β), 4.05 (dd, 1H, J=12.5 Hz, J=2.0 Hz, H-6α), 4.03 (m, 1H, H-3α), 3.70-3.77 (m, 2H, H-3β, H-5α), 3.05 (bs, 1H, OHα), 3.43 (ddd, 1H, J=9.6 Hz, J=J=2.8 Hz, H-5α), 3.29 (bs, 1H, OHβ), 3.19 (dd, 1H, J=J=9.7 Hz, H-4α), 3.18 (dd, 1H, J=9.0 Hz, H-4β), 2.64 (bs, 1H, OHβ), 2.50-2.34 (m, 4H, CHCOα, CHCOβ), 2.22 (ddd, 1H, J=12.4 Hz, J=4.7 Hz, J=2.0 Hz, H-2aβ), 2.15 (ss, 1H, J=12.3 Hz, J=4.4 Hz, H-2eα), 1.81-1.74 (m, 1H, H-1aα), 1.71-1.55 (m, 9H, H-2a, 4CH$_2$α 4CH$_2$β), 1.49-1.38 (m, 8H, 4CH$_2$α, 4CH$_2$β), 1.36-1.25 (m, 24H, 4CH$_3$α, 4CH$_3$β)

Synthesis of 3,6-Di-O-Acyl-2-Deoxy-D-Glucopyranose

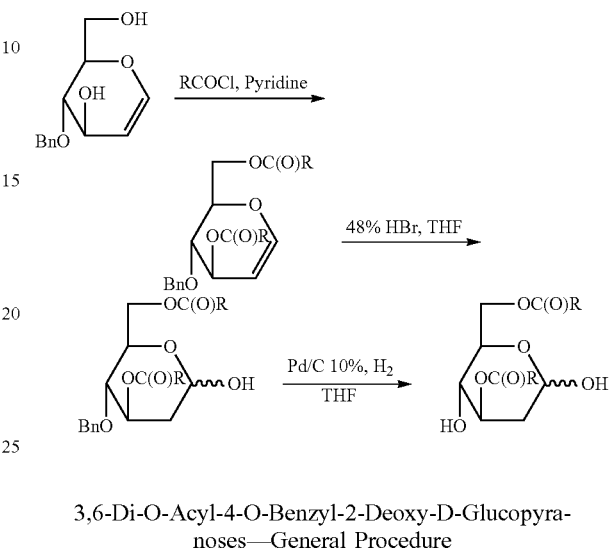

3,6-Di-O-Acyl-4-O-Benzyl-2-Deoxy-D-Glucopyranoses—General Procedure

Solution of 4-O-benzyl-2-deoxy-D-glucopyranose (10 mmol) in a mixture of methylene chloride (30 mL) and pyridine (40 mmol) was prepared, and cooled down to 0° C. Acyl chloride (22 mmol) was slowly added and the mixture was stirred at room temperature overnight. The reaction mixture was diluted with DCM (50 mL) then washed with water (2×30 mL) and dried over anhydrous sodium sulfate. Drying agent and solvents were removed and product was purified by LPC using hexanes:ethyl acetate gradient (0-10% of AcOEt) for elution. Fractions contained product were pooled together, evaporated to dryness and dried under reduced pressure. Following compounds were prepared according to this procedure:

4-O-Benzyl-3,6-Di-O-(2-Ethyl)Butyryl-2-Deoxy-D-Glucopyranose $^1$H NMR (CDCl$_3$, δ) ppm: 7.36-7.29 (m, 5H, Harom.), 6.42 (dd, 1H, J=6.1 Hz, J=1.2 Hz, H-1), 5.44 (dddd, 1H, J=0.7 Hz, J=1.4 Hz, J=3.2 Hz, J=5.4 Hz, H-3), 4.83 (dd, 1H, J=6.1 Hz, J=3.2 Hz, H-2), 4.78 (d, 1H, J=11.2 Hz, 1H, CH$_2$Ph), 4.63 (d, 1H, J=11.2 Hz, 1H, CH$_2$Ph), 4.43 (dd, 1H, J=3.4 Hz, J=12.0 Hz, H-6), 4.37 (dd, 1H, J=5.4 Hz, J=12.0 Hz, H-6'), 4.19 (ddd, 1H, J=8.2 Hz, J=3.4 Hz, J=5.5 Hz, H-5), 3.82 (dd, 1H, J=5.7 Hz, J=7.7 Hz, H-4), 2.31-2.18 (m, 2H, 2CH), 1.71-1.50 (m, 8H, 4CH$_2$), 0.97-0.88 (m, 12H, 4CH$_3$).

4-O-Benzyl-3,6-Di-O-Valeroyl-2-Deoxy-D-Glucopyranose $^1$H NMR (CDCl$_3$, δ), ppm: 7.40-7.31 (m, 5H, Harom.), 6.44 (dd, 1H, J=6.1 Hz, J=1.2 Hz, H-1), 5.45 (dddd, 1H, J=0.6 Hz, J=1.3 Hz, J=3.2 Hz, J=5.7 Hz, H-3), 4.83 (dd, 1H, J=6.1 Hz, J=3.1 Hz, H-2), 4.76 (d, 1H, J=11.5 Hz, CH$_2$Ph), 4.66 (d, 1H, J=11.5 Hz, CH$_2$Ph), 4.42 (dd, 1H, J=3.4 Hz, J=12.0 Hz, H-6), 4.36 (dd, 1H, J=5.3 Hz, J=12.0

Hz, H-6'), 4.20 (ddd, 1H, J=8.2 Hz, J=3.5 Hz, J=5.3 Hz, H-5), 3.83 (dd, 1H, J=5.7 Hz, J=7.9 Hz, H-4), 2.38-2.28 (m, 4H, 2CH$_2$), 1.68-1.58 (m, 4H, 2CH$_2$), 1.44-1.31 (m, 4H, 2CH$_2$), 0.94 (t, J=7.3 Hz, 3H, CH$_3$), 0.93 (t, J=7.3 Hz, 3H, CH$_3$).

4-O-Benzyl-3,6-Di-O-Butyryl-2-Deoxy-D-Glucopyranose $^1$H NMR (CDCl$_3$, δ), ppm: 7.40-7.30 (m, 5H, Harom.), 6.44 (dd, 1H, J=6.1 Hz, J=1.2 Hz, H-1), 5.45 (dddd, 1H, J=0.7 Hz, J=1.3 Hz, J=3.1 Hz, J=5.7 Hz, H-3), 4.83 (dd, 1H, J=6.1 Hz, J=3.1 Hz, H-2), 4.76 (d, 1H, J=11.5 Hz, 1H, CH$_2$Ph), 4.66 (d, 1H, J=11.5 Hz, CH$_2$Ph), 4.42 (dd, 1H, J=3.4 Hz, J=12.0 Hz, H-6), 4.37 (dd, 1H, J=5.3 Hz, J=12.0 Hz, H-6'), 4.20 (ddd, 1H, J=8.3 Hz, J=3.4 Hz, J=5.3 Hz, H-5), 3.83 (dd, 1H, J=5.7 Hz, J=7.9 Hz, H-4), 2.36-2.26 (m, 4H, 2CH$_2$), 1.5 (sext, 4H J=7.4 Hz, 2CH$_2$), 0.98 (t, 6H, J=7.4 Hz, 2CH$_3$).

4-O-Benzyl-3,6-Di-O-Isovaleroyl-2-Deoxy-D-Glucopyranose $^1$H NMR (CDCl$_3$, δ), ppm: 7.37-7.29 (m, 5H, Harom.), 6.42 (dd, 1H, J=6.1 Hz, J=1.2 Hz, H-1), 5.43 (dddd, 1H, J=0.7 Hz, J=1.3 Hz, J=3.2 Hz, J=5.7 Hz, H-3), 4.83 (dd, 1H, J=6.1 Hz, J=3.1 Hz, H-2), 4.74 (d, 1H, J=11.5 Hz, 1H, CH$_2$Ph), 4.66 (d, 1H, J=11.5 Hz, CH$_2$Ph), 4.42 (dd, 1H, J=3.4 Hz, J=12.0 Hz, H-6), 4.34 (dd, 1H, J=5.4 Hz, J=12.0 Hz, H-6'), 4.17 (ddd, 1H, J=8.2 Hz, J=3.4 Hz, J=5.4 Hz, H-5), 3.81 (dd, 1H, J=5.7 Hz, J=7.9 Hz, H-4), 2.17 (d, 4H, J=12.1 Hz, 2CH$_2$), 2.11 (m, 2H, 2CHCO), 0.97 (t, 3H, J=6.4 Hz, CH$_3$).

4-O-Benzyl-3,6-Di-O-Valproyl-2-Deoxy-D-Glucopyranose $^1$H NMR (CDCl$_3$, δ), ppm: 7.37-7.27 (m, 5H, Harom.), 6.41 (dd, 1H, J=6.1 Hz, J=1.1 Hz, H-1), 5.43 (m, 1H, H-3), 4.82 (dd, 1H, J=6.1 Hz, J=3.1 Hz, H-2), 4.77 (d, 1H, J=11.4 Hz, 1H, CH$_2$Ph), 4.63 (d, 1H, J=11.2 Hz, 1H, CH$_2$Ph), 4.43 (dd, 1H, J=3.0 Hz, J=12.1 Hz, H-6), 4.35 (dd, 1H, J=5.5 Hz, J=12.1 Hz, H-6'), 4.17 (ddd, 1H, J=8.1 Hz, J=3.0 Hz, J=5.5 Hz, H-5), 3.81 (dd, 1H, J=5.8 Hz, J=7.9 Hz, H-4), 2.48-2.33 (m, 2H, CHCO), 1.7-1.2 (m, 16H, 8 CH$_2$), 0.93-0.84 (m, 12H, 4 CH$_3$)

4-O-Benzyl-3,6-Di-O-Acyl-2-Deoxy-D-Glucopyranose—General Procedure

47% Hydrobromic acid water solution (0.5 mL, 4.5 mmol) was added to a mixture of 4-O-benzyl-3,6-di-O-acyl-2-deoxy-D-glucopyranose (5 mmol) in tetrahydrofuran (50 mL), and obtained solution was stirred in room temperature. After reaction was completed water (20 mL) followed by sodium carbonate (2.25 mmol, 239 mg) were added and the mixture was stirred for additional 10 min. The reaction mixture was extracted with ethyl acetate (3×30 mL). Combined organic extracts were washed with water until neutral and dried over sodium sulfate. Drying agent and solvents were removed and product was purified by LPC using hexanes:ethyl acetate gradient (0-30% of AcOEt) for elution. Fractions contained product were pooled together, evaporated to dryness and dried under reduced pressure. Following compounds were prepared according to this procedure:

4-O-Benzyl-3,6-Di-O-Butyryl-α-D-Glucopyranose

Yield 63%
$^1$H NMR (CDCl$_3$, δ), ppm: 7.39-7.29 (m, 5H, Harom.), 5.44 (ddd, 1H, J=11.1 Hz, J=8.9 Hz, J=5.1 Hz, H-3), 5.38 (m, 1H, H-1), 4.74 (d, 1H, J=11.2 Hz, CH$_2$Ph), 4.60 (d, 1H, J=11.2 Hz, CH$_2$Ph), 4.39 (dd, 1H, J=2.3 Hz, J=11.9 Hz, H-6), 4.30 (dd, 1H, J=4.3 Hz, J=11.9 Hz, H-6'), 4.17 (ddd, 1H, J=9.8 Hz, J=2.2 Hz, J=4.3 Hz, H-5), 3.55 (dd, 1H, J=J=9.5 Hz, H-4), 2.67 (dd, 1H, J=2.1 Hz, J=3.2 Hz, OH), 2.30 (m, 5H, 2CH$_2$, H-2e), 1.68 (m, 5H, 2CH$_2$, H-2α), 0.98 (t, 3H, J=7.3 Hz, CH$_3$), 0.96 (t, 3H, J=7.3 Hz, CH$_3$)

4-O-Benzyl-3,6-Di-O-Isovaleroyl-D-Glucopyranose

Yield 53%, α:β ratio=10:3
$^1$H NMR (CDCl$_3$, δ), ppm: 7.37-7.25 (m, 10H, Harom.), 5.40 (ddd, 1H, J=11.4 Hz, J=8.6 Hz, J=5.1 Hz, H-3α), 5.36 (m, 1H, H-1α), 5.05 (ddd, 1H, J=11.2 Hz, J=8.9 Hz, J=4.9 Hz, H-3β), 4.93 (m, 1H, H-1β), 4.73 (d, 1H, J=11.1 Hz, CH$_2$Phα), 4.71 (d, 1H, J=11.0 Hz, CH$_2$Ph β), 4.58 (d, 1H, J=11.1 Hz, CH$_2$Phα), 4.57 (d, 1H, J=11.0 Hz, CH$_2$Phβ), 4.41 (dd, 1H, J=2.0 Hz, J=11.9 Hz, H-6β), 4.39 (dd, 1H, J=2.1 Hz, J=11.9 Hz, H-6α), 4.26 (dd, 1H, J=4.3 Hz, J=11.9 Hz, H-6'α), 4.25 (dd, 1H, J=4.8 Hz, J=11.9 Hz, H-6'β), 4.14 (ddd, 1H, J=9.8 Hz, J=2.1 Hz, J=4.3 Hz, H-5α), 3.59 (m, 1H, H-5β), 3.54 (dd, 1H, J=J=9.5 Hz, H-4α), 3.53 (dd, 1H, J=J=9.5 Hz, H-4β), 3.12 (m, 1H, OHβ), 2.62 (m, 1H, OHα), 2.45 (ddd, 1H, J=12.3, Hz, J=5.2 Hz, J=2.4 Hz, H-2eβ), 2.32 (ddd, 1H, J=12.8 Hz, J=5.2 Hz, J=1.6 Hz, H-2eα), 2.23 (m, 4H, 2CHCOα, 2CHCOβ), 2.18-2.04 (m, 8H, 2CH$_2$α, 2CH$_2$β), 1.68 (ddd, 1H, J=J=12.5 Hz, J=3.5 Hz, H-2aα), 1.56 (ddd, 1H, J=J=11.8 Hz, J=9.7 Hz, H-2aβ), 0.95 (t, 24H, J=6.8 Hz, 4CH$_3$α, 4CH$_3$β).

4-O-Benzyl-3,6-Di-O-Valeroyl-D-Glucopyranose

Yield 84%, α:β ratio=3:1
$^1$H NMR (CDCl$_3$, δ), ppm: 7.38-7.26 (m, 10H, Harom.), 5.42 (ddd, 1H, J=11.2 Hz, J=9.0 Hz, J=5.1 Hz, H-3α), 5.38 (m, 1H, H-1α), 5.06 (ddd, 1H, J=11.7 Hz, J=8.5 Hz, J=5.2 Hz, H-3β), 4.94 (m, 1H, H-1β), 4.73 (d, 1H, J=11.2 Hz, CH$_2$Phα), 4.71 (d, 1H, J=11.1 Hz, CH$_2$Phβ), 4.61 (d, 1H, J=11.2 Hz, CH$_2$Phα), 4.59 (d, 1H, J=11.1 Hz, CH$_2$Phβ), 4.41 (dd, 1H, J=2.0 Hz, J=11.9 Hz, H-6β), 4.39 (dd, 1H, J=2.3 Hz, J=11.9 Hz, H-6α), 4.29 (dd, 1H, J=4.4 Hz, J=11.9 Hz, H-6'α), 4.27 (dd, 1H, J=4.7 Hz, J=11.9 Hz, H-6'β), 4.16 (ddd, 1H, J=9.8 Hz, J=2.3 Hz, J=4.3 Hz, H-5α), 3.61 (ddd, 1H, J=9.7 Hz, J=2.1 Hz, J=4.7 Hz, H-5β), 3.55 (dd, 1H, J=J=9.4 Hz, H-4α), 3.54 (dd, 1H, J=J=9.4 Hz, H-4β), 3.14 (d, 1H, J=5.8 Hz, OHβ), 2.65 (m, 1H, OHα), 2.45 (ddd, 1H, J=12.5 Hz, J=5.2 Hz, J=2.0 Hz, H-2eβ), 2.38-2.24 (m, 9H, 2CH$_2$α, 2CH$_2$β, H-2eα), 1.70 (dddd, 1H, J=J=13.1 Hz, J=3.6 Hz, J=1.8 Hz, H-2aα), 1.62 (m, 8H, 2CH$_2$α, 2CH$_2$β), 1.56 (ddd, 1H, J=J=11.6 Hz, J=9.4 Hz, H-2β), 1.36 (m, 8H, 2CH$_2$α, 2CH$_2$β), 0.96-0.88 (m, 12H, 2CH$_3$α, 2CH$_3$β).

4-O-Benzyl-3,6-Di-O-(2-Ethyl)Butyryl-D-Glucopyranose

Yield 69%, α:β ratio=7:3
$^1$H NMR (CDCl$_3$, δ), ppm: 7.34-7.26 (m, 10H, Harom.), 5.40 (ddd, 1H, J=11.1 Hz, J=8.9 Hz, J=5.1 Hz, 1H, H-3α), 5.35 (m, 1H, H-1α), 5.06 (ddd, 1H, J=11.8 Hz, J=8.2 Hz, J=5.0 Hz, H-3β), 4.92 (m, 1H, H-1β), 4.79 (d, 1H, J=10.9 Hz, CH$_2$Phα), 4.77 (d, 1H, J=10.9 Hz, CH$_2$Phβ), 4.58 (d, 1H, J=10.9 Hz, CH$_2$Phα), 4.56 (d, 1H, J=10.9 Hz, CH$_2$Phβ), 4.48 (dd, 1H, J=2.1 Hz, J=11.9 Hz, 1H, H-6α, H-6β), 4.26 (dd, 1H, J=4.3 Hz, J=11.9 Hz, H-6'α), 4.25 (dd, 1H, J=4.5 Hz, J=11.9 Hz, H-6'β), 4.15 (ddd, 1H, J=9.6 Hz, J=2.1 Hz, J=4.4 Hz, H-5α), 3.57 (m, 1H, H-5β), 3.56 (dd, 1H, J=J=9.3 Hz, H-4α), 3.55 (dd, 1H, J=J=9.6 Hz, H-4β), 3.20 (d, 1H, J=5.6 Hz, OHβ), 2.71 (m, 1H, OHα), 2.48 (ddd, 1H, J=12.5, Hz, J=5.3 Hz, J=2.3 Hz, H-20), 2.35 (ddd, 1H, J=12.9 Hz, J=5.1 Hz, J=1.7 Hz, H-2eα), 2.30-2.20 (m, 4H, 2CHCOα, 2CHCOβ), 1.60 (m, 38H, H-2aα, H-2aβ, 4CH₂α, 4CH₂β), 0.88-0.82 (m, 24H, 4CH₃α, 4CH₃β).

4-O-Benzyl-3,6-Di-O-Valproyl-D-Glucopyranose

Yield 78%, α:β ratio=2.5:1
¹H NMR (CDCl₃, δ), ppm: 7.36-7.24 (m, 10H, Harom.), 5.39 (ddd, 1H, J=11.1 Hz, J=9.00 Hz, J=5.0 Hz, H-3α), 5.34 (bs, 1H, H-1α), 5.04 (ddd, 1H, J=12.8 Hz, J=8.3 Hz, J=5.2 Hz, H-3β), 4.93 (m, 1H, H-1β), 4.80 (d, 1H, J=11.0 Hz, CH₂Phα), 4.77 (d, 1H, J=10.9 Hz, CH₂Phβ), 4.57 (d, 1H, J=11.0 Hz, CH₂Phα), 4.56 (d, 1H, J=10.9 Hz, CH₂Ph β), 4.48 (dd, 1H, J=2.1 Hz, J=11.9 Hz, 1H, H-6α, H-6β), 4.27-4.19 (m, 1H, H-6'α, H-6'β), 4.14 (ddd, 1H, J=9.8 Hz, J=2.1 Hz, J=4.1 Hz, H-5α), 3.57 (m, 1H, H-5β), 3.56 (dd, 1H, J=J=9.3 Hz, H-4α), 3.60-3.50 (m, 2H, H-4β, H-53), 3.16 (d, 1H, J=5.4 Hz, OHβ), 2.65 (bs, 1H, OHα), 2.52-2.30 (m, 6H, CHCOα CHCOβ, H-2eα, H-2eβ), 1.70-1.20 (m, 18H, H-2aα, H-2aβ, 4CH₂α, 4CH₂β), 0.94-0.79 (m, 24H, 4CH₃α, 4CH₃β).

3,6-Di-O-Acyl-D-Glucopyranose—General Procedure

Pd/C Degussa type (10% (50% wet)) (0.4 g) was added to the solution of 3,6-di-O-acyl-4-O-benzyl-D-glucopyranose (5 mmol) in ethanol (50 mL). Obtained mixture was hydrogenated at room temperature using Paar apparatus with hydrogen (45 psi). After reaction was completed (TLC control), catalyst was filtered off and the solvent was evaporated to give a crude product. Product was purified by LPC using hexanes:ethyl acetate gradient (0-40% of AcOEt) for elution. Fractions contained product were pooled together, evaporated to dryness and dried under reduced pressure. Following compounds were prepared according to this procedure:

3,6-Di-O-(2-Ethyl)Butyryl-D-Glucopyranose (WP 1234)

Yield 81%, α:β ratio=5:2, [α]$^D$+48°, (c=1.39, chloroform)
¹H NMR (DMSO-d6+D₂O, δ), ppm: 5.15 (d, 1H, J=2.3 Hz, H-1α), 5.06 (ddd, 1H, J=11.5 Hz, J=9.0 Hz, J=5.0 Hz, H-3α), 4.77 (ddd, 1H, J=12.0 Hz, J=9.3 Hz, J=5.3 Hz, H-3(3), 4.75 (m, 1H, H-1β), 4.36 (dd, 1H, J=1.9 Hz, J=11.7 Hz, H-6β, H-6α), 4.08 (dd, 1H, J=5.4 Hz, J=11.7 Hz, H-6'α), 4.06 (dd, 1H, J=6.1 Hz, J=11.6 Hz, H-6'β), 3.88 (ddd, 1H, J=9.8 Hz, J=2.0 Hz, J=5.3 Hz, H-5α), 3.42 (m, 1H, H-5β), 3.30 (dd, 1H, J=J=9.6 Hz, H-4α), 3.25 (dd, 1H, J=J=9.6 Hz, H-4β), 2.11-2.26 (m, 2H, CHCOα, CHCOβ), 2.18 (m, 4H, 2CHα, 2CHβ), 2.04 (ddd, 1H, J=12.2, Hz, J=5.2 Hz, J=2.0 Hz, H-2eβ), 1.93 (ddd, 1H, J=12.3 Hz, J=5.0 Hz, J=1.1 Hz, H-2eα), 1.60-1.41 (m, 17H, 4CH₂α, 4CH₂β, H-2aα), 1.36 (ddd, 1H, J=J=11.8 Hz, J=9.8 Hz, H-2aβ), 0.84 (m, 24H, 4CH₃α, 4CH₃β).

3,6-Di-O-Valeroyl-D-Glucopyranose (WP 1232)

Yield 32%, α:β ratio 4:1, [α]$^D$+60°, (c=1.18, chloroform)
¹H NMR (DMSO-d6+D₂O, δ) ppm: 5.12 (d, 1H, J=2.3 Hz, H-1α), 5.00 (ddd, 1H, J=11.6 Hz, J=9.4 Hz, J=5.1 Hz, H-3α), 4.73 (dd, 1H, J=9.6 Hz, J=1.8 Hz, H-1β), 4.72 (ddd, 1H, J=11.6 Hz, J=8.9 Hz, J=5.1 Hz, H-3β), 4.27 (dd, 1H, J=1.9 Hz, J=11.9 Hz, H-6β), 4.24 (dd, 1H, J=2.0 Hz, J=11.7 Hz, H-6α), 4.07 (dd, 1H, J=5.5 Hz, J=11.7 Hz, H-6'α), 4.03 (dd, 1H, J=5.9 Hz, J=11.9 Hz, H-6'β), 3.85 (ddd, 1H, J=9.7 Hz, J=1.9 Hz, J=5.4 Hz, H-5α), 3.40 (m, 1H, H-5β), 3.27 (dd, 1H, J=J=9.6 Hz, H-4α), 3.23 (dd, 1H, J=J=9.4 Hz, H-4β), 2.26 (m, 8H, 2CH₂α, 2CH₂β), 2.00 (ddd, 1H, J=12.0, Hz, J=5.2 Hz, J=1.8 Hz, H-2eβ), 1.90 (ddd, 1H, J=12.4 Hz, J=5.2 Hz, J=0.8 Hz, H-2eα), 1.48 (m, 9H, 2CH₂α, 2CH₂β, H-2aα), 1.33 (ddd, 1H, J=J=12.0 Hz, J=10 Hz, H-2β), 1.26 (m, 8H, 2CH₂α, 2CH₂β), 0.84 (t, J=7.4 Hz, 12H, 2CH₃α, 2CH₃β).

3,6-Di-O-Isovaleroyl-α-D-Glucopyranose (WP1263)

Yield 51%, [α]$^D$+57°, (c=1.20, chloroform)
¹H NMR (DMSO-d6, δ), ppm: 6.43 (dd, 1H, J=4.0 Hz, J=1.3 Hz, 1-OH), 5.26 (d, 1H, J=6.6 Hz, 4-OH), 5.14 (m, 1H, H-1), 5.03 (ddd, 1H, J=11.6 Hz, J=9.4 Hz, J=5.0 Hz, H-3), 4.28 (dd, 1H, J=1.9 Hz, J=11.7 Hz, H-6), 4.06 (dd, 1H, J=5.5 Hz, J=11.7 Hz, H-6'), 3.86 (ddd, 1H, J=9.8 Hz, J=1.8 Hz, J=5.4 Hz, H-5), 3.28 (dd, 1H, J=J=9.5 Hz, J=6.5 Hz, H-4), 2.15 (m, 4H, 2CH₂), 2.04-1.87 (m, 3H, 2CH₂, H-2e), 1.48 (dd, 1H, J=J=12.4 Hz, H-2α), 0.89 (d, 6H, J=6.6 Hz, 2CH₃), 0.88 (d, 6H, J=6.6 Hz, 2CH₃).

3,6-Di-O-Butyryl-α-D-Glucopyranose (WP1213)

Yield 89%, [α]$^D$+66°, (c=1.23, chloroform)
¹H NMR (DMSO-d6+D₂O, δ), ppm: 5.15 (d, 1H, J=2.0 Hz, H-1), 5.03 (ddd, 1H, J=11.7 Hz, J=9.3 Hz, J=5.1 Hz, H-3), 4.27 (dd, 1H, J=2.0 Hz, J=11.7 Hz, H-6), 4.09 (dd, 1H, J=5.6 Hz, J=11.7 Hz, H-6'), 3.87 (ddd, 1H, J=9.9 Hz, J=1.9 Hz, J=5.7 Hz, H-5), 3.30 (dd, 1H, J=J=9.5 Hz, H-4), 2.27 (m, 4H, 2CH₂), 1.93 (ddd, 1H, J=11.8, Hz, J=5.0 Hz, J=1.0 Hz, H-2e), 1.60-1.46 (m, 5H, 2CH₂, H-2α), 0.89 (t, 3H, J=7.4 Hz, CH₃), 0.88 (t, 3H, J=7.4 Hz, CH₃).

3,6-Di-O-Valproyl-D-Glucopyranose (WP 1506)

Yield 84%,
¹H NMR (CDCl₃, δ), ppm: 5.39 (bs, 1H, H-1α), 5.24 (ddd, 1H, J=11.7 Hz, J=9.3 Hz, J=5.2 Hz, H-3α), 4.97-4.85 (m, 2H, H-1β, H-3β), 4.47 (dd, 1H, J=12.2 Hz, J=4.0 Hz, H-6β), 4.44 (dd, 1H, J=12.1 Hz, J=4.0 Hz, H-6α), 4.39 (dd, 1H, J=12.1 Hz, J=2.5 Hz, H-6'α), 4.37 (dd, 1H, J=12.2 Hz, J=2.1 Hz, H-6'β), 4.04 (ddd, 1H, J=9.7 Hz, J=3.8 Hz, J=2.6 Hz, H-5α), 3.53-3.39 (m, 3H, H-4α, H-4β, H-5β), 3.22 (d, 1H, J=5.7 Hz, OHβ), 2.97 (d, 1H, J=4.7 Hz, OHα), 2.89 (d, 1H, J=3.9 Hz, OHβ), 2.75 (dd, 1H, J=J=2.6 Hz, OHα), 2.51-2.30 (m, 3H, CHCOα, CHCOβ, H-2eβ), 2.20 (ddd, 1H, J=12.9 Hz, J=5.2 Hz, J=1.0 Hz, H-2eα), 1.78-1.22 (m, 18H, H-2aα, H-2aβ, 4CH₂α, 4CH₂β), 0.90 (t, 24H, J=7.2 Hz, 4CH₃α, 4CH₃β).

Synthesis of 4.6-Di-O-Acyl-2-Deoxy-D-Glucopyranose

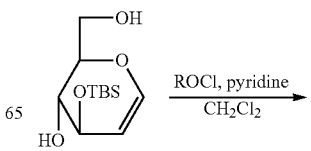

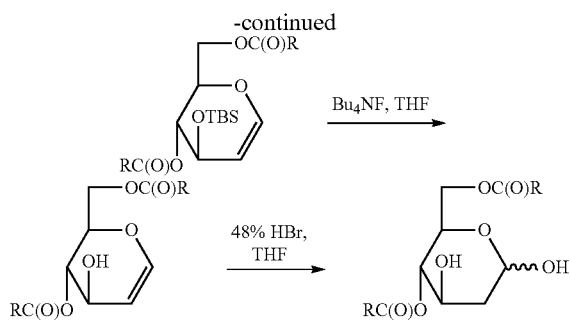

3-O-Tert-Butyldimethylsilyl-4,6-Di-O-Acyl-2-Deoxy-D-Glucopyranose—General Procedure Solution of 3-O-tert-butyldimethylsilyl-2-deoxy-D-glucopyranose (10 mmol) and pyridine (40 mmol) in DCM (30 mL) was prepared and cooled down to 0° C. Acyl chloride (22 mmol) was slowly added and obtained reaction mixture was stirred at room temperature overnight. The mixture was diluted with dichloromethane (50 mL), washed with water (2×30 mL) and dried over anhydrous sodium sulfate. Drying agent and solvents were removed and product was purified by LPC using hexanes:ethyl acetate gradient (0-20% of AcOEt) for elution. Fractions contained product were pooled together, evaporated to dryness and dried under reduced pressure. Following compounds were prepared according to this procedure:

3-O-Tert-Butyldimethylsilyl-4,6-Di-O-Butyryl-2-Deoxy-D-Glucopyranose

Yield 70%, $[\alpha]^{20}=-19.49$ (c=1, chloroform).
$^1$H NMR (CDCl$_3$, δ) ppm: 6.37 (d, J=6.2 Hz, J=1.1 Hz, 1H, H-1), 5.08 (m, 1H, H-4), 4.78 (ddd, 1H, J=6.2 Hz, J=3.5 Hz, J=0.6 Hz, H-2), 4.43 (m, 1H, H-6), 4.27-4.15 (m, 3H, H-3, H-5, H-6'), 2.34 (m, 4H, 2 CH$_2$), 1.68 (m, 4H, 2 CH$_2$), 0.98 (t, J=7.4 Hz, 3H, CH$_3$), 0.97 (t, J=7.4 Hz, 3H, CH$_3$), 0.90 (s, 6H, t-Bu), 0.11, 0.10 (2s, 3H, Me$_2$Si)

3-O-Tert-Butyldimethylsilyl-4,6-Di-O-Valeroyl-2-Deoxy-D-Glucopyranose

Yield 85%, $[\alpha]^{20}=-21.69$ (c=1, chloroform)
$^1$H NMR (CDCl$_3$, δ) ppm: 6.35 (d, J=6.2 Hz, J=1.0 Hz, 1H, H-1), 5.04 (m, 1H, H-4), 4.76 (ddd, 1H, J=6.2 Hz, J=3.6 Hz, J=0.6 Hz, H-2), 4.41 (m, 1H, H-6), 4.25-4.13 (m, 3H, H-3, H-5, H-6'), 2.34 (m, 4H, 2 CH$_2$), 1.61 (m, 4H, 2 CH$_2$), 1.35 (m, 4H, 2 CH$_2$), 0.91 (t, J=7.4 Hz, 3H, CH$_3$), 0.91 (t, J=7.4 Hz, 3H, CH$_3$), 0.88 (s, 9H, t-Bu), 0.09, 0.08 (2s, 3H ea, Me$_2$Si)

3-O-tert-butyldimethylsilyl-4,6-di-O-(2-ethyl)butyryl-2-deoxy-D-glucopyranose Yield 98%, $[\alpha]^{20}=-20.32$ (c=1, chloroform)
$^1$H NMR (CDCl$_3$, δ) ppm: 6.35 (dd, 1H, J=6.4 Hz, H-1), 5.02 (ddd, J=J=3.7 Hz, J=1.1 Hz, 1H, H-4), 4.83 (ddd, 1H, J=6.1 Hz, J=4.5 Hz, J=1.2 Hz, H-2), 4.54 (dd, 1H, J=12.1 Hz, J=8.1 Hz, 1H, H-6), 4.34 (m, 1H, H-3), 4.24 (dd, 1H, 1H, J=12.0 Hz, J=3.2 Hz, H-6'), 4.04 (m, 1H, H-5), 2.30 (m, 2H, 2 CHCO), 1.65 (m, 8H, 4 CH$_2$), 0.91 (t, J=7.4 Hz, 12H, 4 CH$_3$), 0.13 (s, 9H, t-Bu), 0.12, 0.08 (2s, 3H ea, Me$_2$Si), 0.08

3-O-Tert-Butyldimethylsilyl-4,6-Di-O-Valproyl-2-Deoxy-D-Glucopyranose (Yield 79.7%)
$^1$H NMR (CDCl$_3$, 300 MHz, δ) ppm: 6.36 (d, 1H, J=6.3 Hz, H-1), 4.96 (ddd, 1H, J=3.5 Hz, J=3.5 Hz, J=1.1 HZ, H-4), 4.81 (ddd, 1H, J=6.0 Hz, J=4.5 Hz, J=1.1 Hz, H-2), 4.51 (dd, 1H, J=12.0 Hz, J=8.2 Hz, H-6), 4.34-4.26 (m, 1H, H-5), 4.20 (dd, 1H, J=12.0 Hz, J=3.2 Hz, H-6'), 3.96-4.02 (m, 1H, H-3), 2.50-2.35 (m, 2H, CHCO), 1.73-1.23 (m, 16H, 8CH$_2$), 0.92 (t, 6H, J=7.2 Hz, 2CH$_3$), 0.89 (t, 6H, J=7.2 Hz, 2CH$_3$), 0.89 (s, 9H, t-BuSi), 0.11, 0.10 (2s, 3H ea, MeSi)

4,6-Di-O-Acyl-2-Deoxy-D-Glucopyranose—General Procedure

Solution of 4,6-di-O-acyl-3-tert-butyldimethylsilyl-2-deoxy-D-glucopyranose (5 mmol) in THF (50 mL) was prepared. 1M Solution of tetrabutylammonium fluoride in tetrahydrofurane (5 ml, 5 mmol) was added and the mixture was stirred in room temperature overnight. After reaction was completed the reaction mixture was poured into the water (150 mL), and water solution was extracted with ethyl acetate (3×30 mL). Combined organic extracts were washed with water until neutral and dried over anhydrous sodium sulfate. Drying agent and solvents were removed and product was purified by LPC using hexanes:ethyl acetate gradient (0-30% of AcOEt) for elution. Fractions contained product were pooled together, evaporated to dryness and dried under reduced pressure. Following compounds were prepared according to this procedure:

4,6-Di-O-Butyryl-2-Deoxy-D-Glucopyranose

Yield 70%,
$^1$H NMR (CDCl$_3$, δ) ppm: 6.42 (dd, J=6.1 Hz, J=1.4 Hz, 1H, H-1), 4.99 (dd, J=6.4 Hz, J=9.0 Hz, 1H, H-4), 4.88 (dd, J=6.1 Hz, J=2.8 Hz, 1H, H-2), 4.39 (dd, J=5.2 Hz, J=12.3 Hz, 1H, H-6), 4.33 (ddd, J=6.4 Hz, J=2.6 Hz, J=1.4 Hz, 1H, H-3), 4.30 (dd, J=2.6 Hz, J=12.3 Hz, 1H, H-6'), 4.14 (ddd, J=9.0 Hz, J=5.3 Hz, J=2.6 Hz, 1H, H-5), 2.65 (m, 1H, OH), 2.38 (t, J=7.4 Hz, 2H, CH$_2$), 2.35 (t, J=7.4 Hz, 2H, CH$_2$), 1.69 (sext, J=7.4 Hz, 2H, CH$_2$), 1.67 (sext, J=7.4 Hz, 2H, CH$_2$), 0.98 (t, J=7.4 Hz, 3H, CH$_3$), 0.96 (t, J=7.4 Hz, 3H, CH$_3$)

4,6-Di-O-Valeroyl-2-Deoxy-D-Glucopyranose

Yield 25%, $[\alpha]^{20}=43.72$ (c=1, chloroform)
$^1$H NMR (CDCl$_3$, δ) ppm: 6.42 (dd, J=6.1 Hz, J=1.5 Hz, 1H, H-1), 4.99 (dd, J=6.3 Hz, J=9.0 Hz, 1H, H-4), 4.88 (dd, J=6.1 Hz, J=2.8 Hz, 1H, H-2), 4.39 (dd, J=5.2 Hz, J=12.3 Hz, 1H, H-6), 4.33 (ddd, J=6.3 Hz, J=2.7 Hz, J=1.5 Hz, 1H, H-3), 4.30 (dd, J=2.6 Hz, J=12.3 Hz, 1H, H-6'), 4.14 (ddd, J=8.9 Hz, J=5.2 Hz, J=2.6 Hz, 1H, H-5), 2.65 (m, 1H, OH), 2.40 (t, J=7.4 Hz, 2H, CH$_2$), 2.37 (t, J=7.4 Hz, 2H, CH$_2$), 1.70-1.58 (m, 4H, 2CH$_2$), 1.44-1.32 (m, 4H, 2CH$_2$), 0.94 (t, J=7.3 Hz, 3H, CH$_3$), 0.93 (t, J=7.4 Hz, 3H, CH$_3$).

4,6-Di-O-(2-Ethyl)Butyryl-2-Deoxy-D-Glucopyranose

Yield 45%, $[\alpha]^{20}=60.16$ (c=1, chloroform)
$^1$H NMR (CDCl$_3$, δ) ppm: 6.39 (dd, 1H, J=6.1 Hz, J=1.4 Hz, H-1), 4.99 (dd, 1H, J=6.2 Hz, J=8.9 Hz, H-4), 4.85 (dd, 1H, J=6.1 Hz, J=2.8 Hz, H-2), 4.46 (dd, 1H, J=2.4 Hz, J=12.1 Hz, H-6), 4.3) (m, 1H, H-3), 4.23 (dd, 1H, J=5.3 Hz, J=12.1 Hz, H-6'), 4.13 (ddd, 1H, J=8.6 Hz, J=5.3 Hz, J=2.4

Hz, H-5), 2.80 (m, 1H, OH), 2.27 (m, 2H, 2CHCO), 1.70-1.45 (m, 8H, 4CH$_2$), 0.95-0.85 (m, 12H, 4CH$_3$).

4,6-Di-O-Valproyl-2-Deoxy-D-Glucopyranose (Yield 93.8%)
$^1$H NMR (CDCl$_3$, 300 MHz, δ) ppm: 6.40 (dd, 1H, J=6.0 Hz, J=1.3 Hz, H-1), 4.97 (dd, 1H, J=8.9 Hz, J=6.2 Hz, H-4), 4.85 (dd, 1H, J=6.1 Hz, J=2.8 Hz, H-2), 4.47 (dd, 1H, J=12.0 Hz, J=2.1 Hz, H-6), 4.30 (bs, 1H, H-3), 4.24-4.09 (m, 2H, H-5, H-6') 2.83 (bs, 1H, OH), 2.50-2.36 (m, 2H, CHCO), 1.70-1.21 (m, 16H, 8CH$_2$), 0.95-0.85 (m, 12H, 4CH$_3$)

4,6-Di-O-Acyl-2-Deoxy-D-Glucopyranose—General Procedure

47% Hydrobromic acid (0.5 mL) was added to a solution of 4,6-di-O-acyl-2-deoxy-D-glucopyranose (5 mmol, 4.5 mmol) in THF (50 mL), and the mixture was stirred at room temperature. After reaction was completed water (25 mL) followed by sodium carbonate (2.25 mmol, 239 mg) were added and the mixture was stirred for additional 10 min. The reaction mixture was extracted with ethyl acetate (3×30 mL). Combined organic extracts were washed with water until neutral and dried over sodium sulfate. Drying agent and solvents were removed and product was purified by LPC using methylene chloride:methanol gradient (0-40% of MeOH) for elution. Fractions contained product were pooled together, evaporated to dryness and dried under reduced pressure. Following compounds were prepared according to this procedure:

4,6-Di-O-Valeroyl-2-Deoxy-D-Glucopyranose (WP1233)

Yield 79%, α:β ratio=10:1, [α]$^D$+60°, (c=1.39, chloroform)
$^1$H NMR (DMSO-d6+D$_2$O, δ) ppm: 5.15 (dd, 1H, J=2.4 Hz, H-1α), 4.70 (dd, 1H, J=9.5 Hz, J=1.5 Hz, H-1β), 4.58 (dd, 1H, J=J=9.5 Hz, H-4α), 4.51 (dd, 1H, J=J=9.5 Hz, H-4β), 4.00 (dd, 2H, J=12.1 Hz, J=5.1 Hz, H-6α, H-6β), 3.91 (m, 3H, H-6'α, H-6'β, H-5α), 3.83 (ddd, 1H, J=11.6 Hz, J=9.2 Hz, J=5.0 Hz, H-3α), 3.61 (ddd, 1H, J=11.6 Hz, J=9.2 Hz, J=5.0 Hz, H-3β), 3.50 (m, 1H, H-53), 2.28 (t, 4H, J=6.8 Hz, CH$_2$α, CH$_2$β), 2.24 (t, 4H, J=7.4 Hz, CH$_2$α, CH$_2$β), 1.99 (ddd, 1H, J=12.4 Hz, J=5.2 Hz, J=1.9 Hz, H-2eβ), 1.88 (dd, 1H, J=12.2 Hz, J=5.2 Hz, H-2eα), 1.58-1.38 (m, 10H, 2 CH$_2$α, 2 CH$_2$β, H-2aα, H-2β), 1.26 (m, 8H, 2 CH$_2$α, 2 CH$_2$β), 0.84 (t, 12H, J=7.5 Hz, 2CH$_3$α, 2CH$_3$β).

4,6-Di-O-Butyryl-2-Deoxy-D-Glucopyranose (WP1214)

Yield 78%, α:β ratio=10:1, [α]$^D$+62°, (c=1.36, chloroform)
$^1$H NMR (DMSO-d6+D$_2$O, δ) ppm: 5.18 (dd, 1H, J=2.4 Hz, H-1α), 4.72 (dd, 1H, J=9.8 Hz, J=1.8 Hz, H-1β), 4.61 (dd, 1H, J=J=9.6 Hz, H-4α), 4.54 (dd, 1H, J=J=9.5 Hz, 1H, H-4β), 4.04 (dd, 2H, J=12.1 Hz, J=5.0 Hz, H-6α, H-6β), 3.99-3.89 (m, 3H, H-6'α, H-6'β, H-5α), 3.86 (ddd, 1H, J=11.6 Hz, J=9.3 Hz, J=5.0 Hz, H-3α), 3.63 (ddd, 1H, J=10.6 Hz, J=8.9 Hz, J=4.9 Hz, H-3β), 3.52 (m, 1H, H-5β), 2.33-2.22 (m, 8H, 2 CH$_2$α, 2 CH$_2$β), 2.02 (ddd, 1H, J=12.3 Hz, J=5.2 Hz, J=2.1 Hz, H-2eβ), 1.91 (ddd, 1H, J=12.9 Hz, J=5.1 Hz, J=0.8 Hz, H-2eα), 1.54 (m, 9H, 2 CH$_2$α, 2 CH$_2$β, H-2aα), 1.49 (ddd, 1H, J=J=12.0 Hz, J=10.0 Hz, H-2β), 0.89 (t, 6H, J=7.4 Hz, 6H, CH$_3$α, CH$_3$β), 0.99 (t, 6H, J=7.4 Hz, CH$_3$α, CH$_3$β).

4,6-Di-O-(2-Ethyl)Butyryl-2-Deoxy-α-D-Glucopyranose (WP1241)

Yield 78%, [α]$^D$+74°, (c=1.21, chloroform)
$^1$H NMR (DMSO-d6+D$_2$O, δ) ppm: 5.18 (dd, 1H, J=2.2 Hz, H-1), 4.61 (dd, 1H, J=J=9.4 Hz, H-4), 4.13 (d, 1H, J=11.3 Hz, H-6), 3.99-3.86 (m, 2H, H-6', H-5), 3.85 (ddd, 1H, J=11.5 Hz, J=9.4 Hz, J=5.0 Hz, H-3α), 2.20 (m, 2H, 2 CHCO), 1.91 (dd, 1H, J=12.8 Hz, J=5.1 Hz, H-2e), 1.52 (m, 9H, 4CH$_2$, H-2α), 0.84 (m, 12H, 4CH$_3$).

4.6-Di-O-Valproyl-2-Deoxy-D-Glucopyranose (WP1483)

(Yield %), α:β ratio=3:1
$^1$H NMR (CDCl$_3$, 300 MHz, δ) ppm: 5.39 (bs, 1H, H-1α), 4.92-4.85 (m, 1H, H-1β), 4.77 (dd, 1H, J=J=9.6 Hz, H-4α), 4.73 (dd, 1H, J=J=9.6 Hz, H-4β), 4.41 (dd, 1H, J=12.0 Hz, J=2.0 Hz, H-6α), 4.37 (dd, 1H, J=12.1 Hz, J=2.0 Hz, H-6β), 4.20-4.06 (m, H-3α, H-5α, H-6'β), 4.02 (dd, 1H, J=12.1 Hz, J=4.4 Hz, H-6'α), 3.87-3.74 (m, 1H, H—H-3β), 3.65 (ddd, 1H, J=9.0 Hz, J=5.4 Hz, J=2.2 Hz, H-5β), 3.22 (d, 1H, J=6.3 Hz, OH-β), 2.78 (d, 1H, J=5.3 Hz, OH-β), 2.62 (dd, 1H, J=2.9 Hz, J=2.3 Hz, OH-α), 2.50 (d, 1H, J=5.3 Hz, OH-α), 2.47-2.35 (m, 5H, CHCOα, CHCOβ, H-2eβ), 2.27 (ddd, 1H, J=13.6 Hz, J=5.2 Hz, J=1.0 Hz, H-2eα), 1.77-1.20 (m, 18H, H-2aα, H-2aβ, 4CH$_2$α, 4CH$_2$β), 0.94-0.85 (m, 24H, 4CH$_3$α, 4CH$_3$β).

Activity

In the first set of assays, IC$_{50}$ values were determined for each compound after 72 hours of drug exposure in each of the tumor cell lines. Cell lines tested include D54, U87, Panc-1, AsPc-1, Colo357-FG, L3.6, H226, H352, H441 cell lines.

U87 is a human primary glioblastoma cell line formally known as U-87 MG. It has epithelial morphology, and was obtained from a 44 years old female patient with stage four cancer. U-87 MG can be obtained from the American Type Culture Collection (ATCC) where it is known by the accession number HTB-14. The entire sequence of the genome of U-87 MG has recently been published in PLoS Genetics, 2010 January; 6(1): e1000832. This is a hypodiploid human cell line with the modal chromosome number of 44 occurring in 48% of cells. The rate of higher ploidy was 5.9%. Twelve markers were common to all cells, including der(1) t(1;3) (p22;q21), der(16)t(1;16) (p22;p12), del(9) (p13) and nine others. The marker der(1) had two copies in most cells. There was only one copy of normal X. N1, N6 and N9 were not found.

COLO 357 FG is continuous human cell line, COLO 357, with exceptional characteristics was derived from a metastasis of a pancreatic adenocarcinoma. COLO 357 grew as an adhering monolayer with a cell doubling time of 21 h and grew with 10% clonal efficiency in soft agar. COLO 357 cells had numerous lamellar inclusions. The cells elaborated the pancreatic enzymes trypsin, elastase and chymotrypsin. COLO 357 also secreted appreciable amounts of carcinoembryonic antigen and human chorionic gonadotropin. COLO 357 had a chromosome mode of 53 with 20 identifiable Giemsa-banded marker chromosomes. Nine nucleolar organizing regions were found by silver-stained metaphase preparations. COLO 357 has been "fingerprinted" for seven allelic isozymes.

Panc-1 is a human pancreatic cancer cell line. It has epithelial morphology and was obtained from a 56 years old male caucasian patient. Chromosome studies indicate a modal number of 63 with 3 distinct marker chromosomes and a small ring chromosome. This is a hypertriploid human cell line. The modal chromosome number was 61, occurring in 32% of cells. However, cells with 63 chromosomes also occurred at a high frequency (22%). The rate of cells with higher ploidies was 8.5%.

AsPc-1 cell line was derived from nude mouse xenografts initiated with cells from the ascites of a 62 years old female Caucasian patient with cancer of the pancreas.

L3.6 is a highly metastatic human pancreatic cancer cell line.

H226 is a squamous cell carcinoma cell line. The morphology of the disease is epithelial and was collect from lung tissues (pleural effusion of a male patient with mesothelioma.

H441 is a human lung adenocarcinoma epithelial cell line.

All cell lines were maintained in respective growth media at 37° C., 5% $CO_2$ and 98% humidity. Cells were treated with the compounds and all drug concentrations were diluted so that the final concentration of DMSO is 0.5%. The cytotoxic effect was measured by the MTS Assay (Tetrazolium), which is a colorimetric method for determining the number of viable cells. After the 72 hours of incubation with drug, Promega's MTS reagent were added to the cells according to manufacturer's instructions and incubated for 2 hours. The plates were read at 490 nm and the resulting data graphed with GraphPad Prism 5 software.

$IC_{50}$ was calculated, which is approximate equivalent of $IG_{50}$ (concentration at which 50% growth inhibition is measured). The individual $IC_{50}$ values (72 hours drug exposure) are shown in Table 1. The $IC_{50}$ values represent 100% of the drug concentration.

TABLE 1

Chemical Structures Of 2-Dg Esters And Their Vitro Activity

| No | Structure | Brain Tumor U87 | Pancreatic Cancer Colo357-FG |
|---|---|---|---|
| WP1213 | 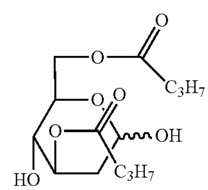 | 0.24 mM | 0.38 mM |
| WP1214 | 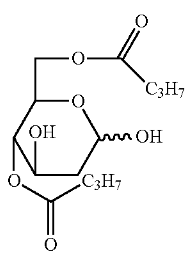 | 0.30 mM | 0.44 mM |
| WP1216 | 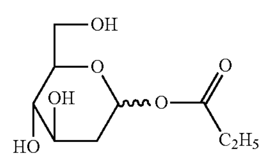 | 3.58 mM | — |
| WP1217 | 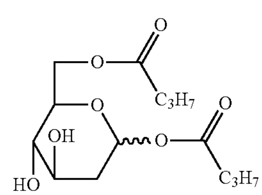 | 2.33 mM | — |
| WP1231 | 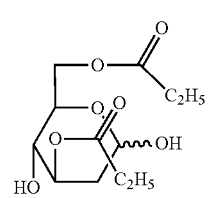 | 0.38 mM | 0.55 mM |

TABLE 1-continued

Chemical Structures Of 2-Dg Esters And Their Vitro Activity

| No | Structure | Brain Tumor U87 | Pancreatic Cancer Colo357-FG |
|---|---|---|---|
| WP1232 | 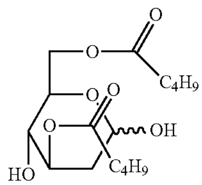 | 0.25 mM | 0.49 mM |
| WP1233 | 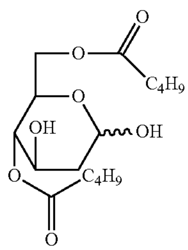 | 0.20 mM | 0.23 mM |
| WP1234 | 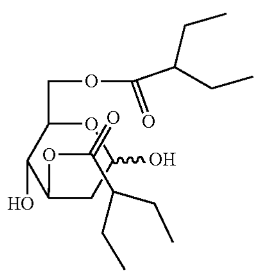 [SMILES: CCC(CC)C(=O)OCC1OC(O)CC(OC(=O)C(CC)CC)C1O] | 0.055 mM | 0.10 mM |
| WP1241 | 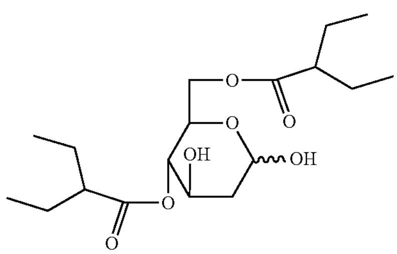 | 0.123 mM | 0.28 mM |
| WP1242 | 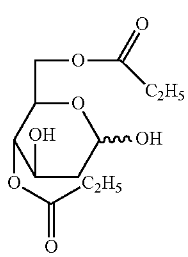 | 0.490 mM | 6.38 mM |
| WP1261 | 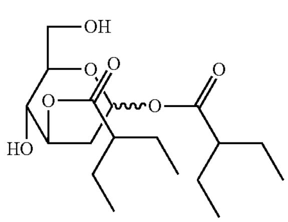 [SMILES: CCC(CC)C(=O)OC1CC(OC(=O)C(CC)CC)C(O)C(CO)O1] | 0.741 mM | 0.34 mM |

TABLE 1-continued

Chemical Structures Of 2-Dg Esters And Their Vitro Activity

| No | Structure | Brain Tumor U87 | Pancreatic Cancer Colo357-FG |
|---|---|---|---|
| WP1262 | 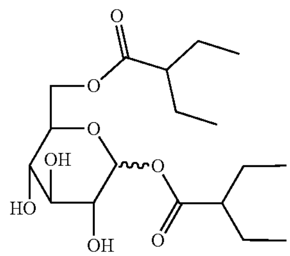 | 0.264 mM | 0.21 mM |
| WP1263 | 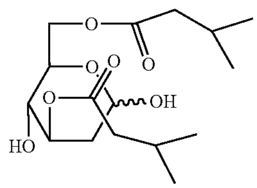 [SMILES: CC(C)CC(=O)OCC1OC(O)CC(OC(=O)CC(C)C)C1O] | 0.037 mM | 0.16 mM |
| WP1317 | 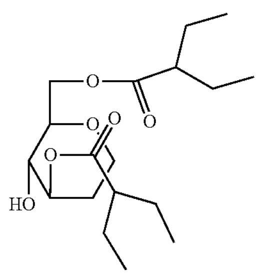 [SMILES: CCC(CC)C(=O)OCC1OCCC(OC(=O)C(CC)CC)C1O] | 2.10 mM | 2.1 mM |
| WP1319 | 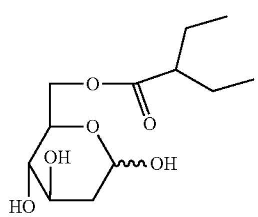 | 3.0 mM | 1.70 mM |
| WP1342 | 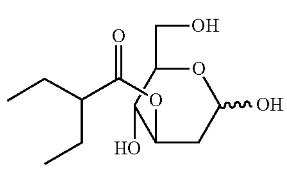 [SMILES: CCC(CC)C(=O)OC1CC(O)OC(CO)C1O] | 2.4 mM | 13.2 mM |
| WP1343 | 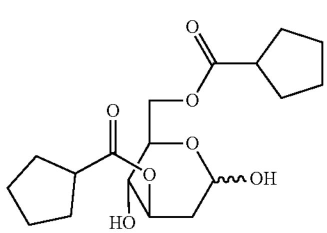 [SMILES: O=C(OCC1OC(O)CC(OC(=O)C2CCCC2)C1O)C1CCCC1] | 0.109 mM | 0.75 mM |

TABLE 1-continued

Chemical Structures Of 2-Dg Esters And Their Vitro Activity

| No | Structure | Brain Tumor U87 | Pancreatic Cancer Colo357-FG |
|---|---|---|---|
| WP1357 | 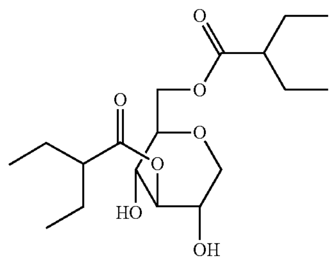 [SMILES: CCC(CC)C(=O)OCC1OCC(O)C(OC(=O)C(CC)CC)C1O] | — | 0.54 mM |
| WP1474 | 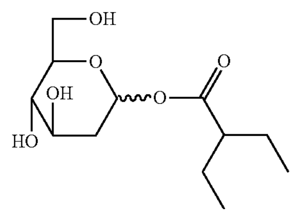 | 2.4 mM | — |
| WP1490 | 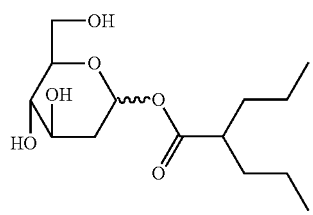 | 2.4 mM | 2.0 mM |
| WP1512 | 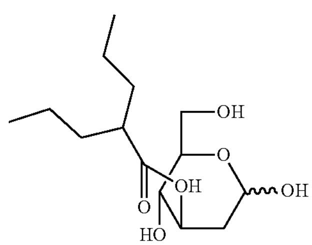 [SMILES: CCCC(CCC)C(=O)OC1CC(O)OC(CO)C1O] | 0.74 mM | — |
| WP1513 | 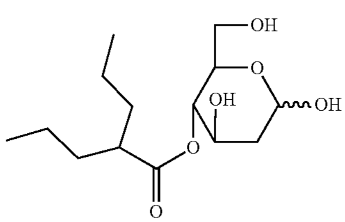 | 1.2 mM | 1.2 mM |
| WP1491 | 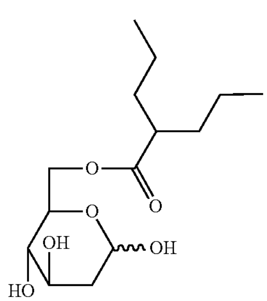 | 2.1 mM | — |

TABLE 1-continued

Chemical Structures Of 2-Dg Esters And Their Vitro Activity

| No | Structure | Brain Tumor U87 | Pancreatic Cancer Colo357-FG |
|----|-----------|-----------------|------------------------------|
| WP1489 | 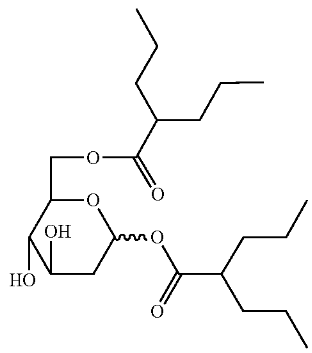 | | |
| WP1506 | 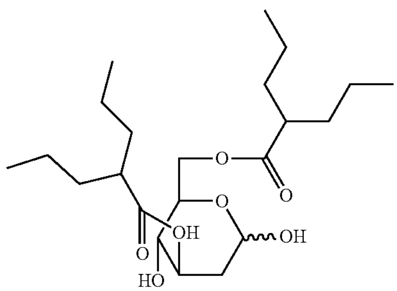 [SMILES: CCCC(CCC)C(=O)OCC1OC(O)CC(OC(=O)C(CCC)CCC)C1O] | | |
| WP1483 | 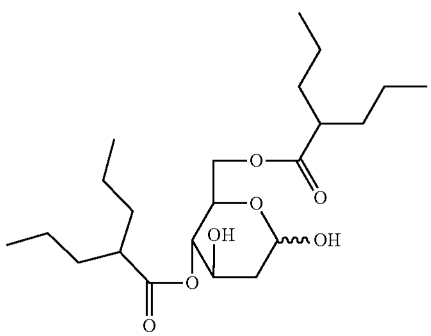 | | |

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A method of treating a proliferative disease chosen from squamous cell carcinoma and lung adenocarcinoma by inhibiting glycolysis in glycolytic tumor cells in a patient in need thereof comprising administering a therapeutically effective amount of one or more compounds of the Formula I:

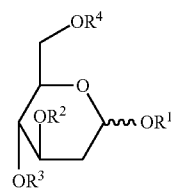

or a salt, ester or prodrug thereof, wherein:
each $R^1$, $R^2$, $R^3$ and $R^4$ are independently H, or $COR^5$;
at least one of $R^1$, $R^2$, $R^3$ and $R^4$ is $COR^5$; and each $R^5$ is independently selected from the group $C_3$-$C_{10}$ straight- or branched-chain alkyl, $C_4$-$C_{10}$ alkylcycloalkyl, and $C_3$-$C_{10}$ cycloalkyl.

2. The method of claim 1, wherein $R^2$ and $R^3$ are $COR^5$.

3. The method of claim 1, wherein $R_5$ is independently selected from the group $C_3$-$C_7$ straight- or branched-chain alkyl, $C_4$-$C_{10}$ alkylcycloalkyl, and $C_3$-$C_7$ cycloalkyl.

4. The method of claim 1, wherein the compound is

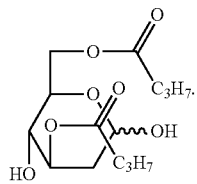

5. The method of claim 1, wherein the compound is

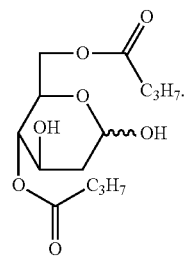

6. The method of claim 1, wherein the compound is

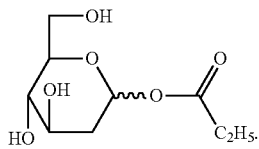

7. The method of claim 1, wherein the compound is

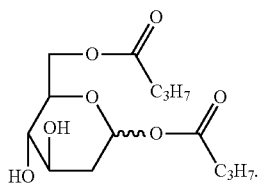

8. The method of claim 1, wherein the compound is

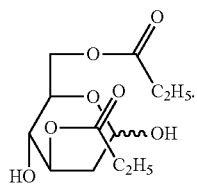

9. The method of claim 1, wherein the compound is

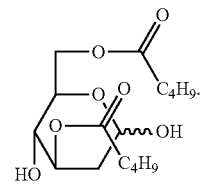

10. The method of claim 1, wherein the compound is

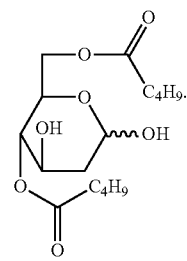

11. The method of claim 1, wherein the compound is

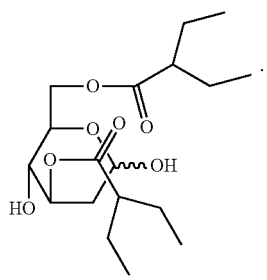 [SMILES: CCC(CC)C(=O)OCC1OC(O)CC(OC(=O)C(CC)CC)C1O]

12. The method of claim 1, wherein the compound is

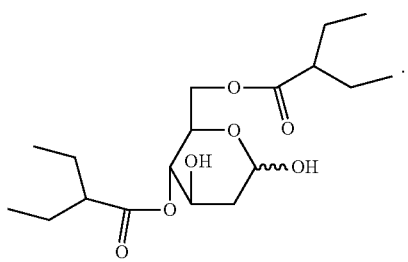

13. The method of claim 1, wherein the compound is

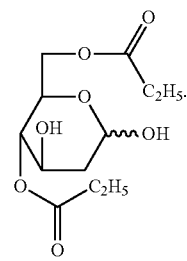

14. The method of claim 1, wherein the compound is

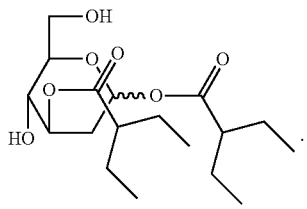 [SMILES: CCC(CC)C(=O)OC1CC(OC(=O)C(CC)CC)C(O)C(CO)O1]

15. The method of claim 1, wherein the compound is

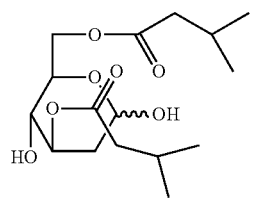

16. The method of claim 1, wherein the compound is

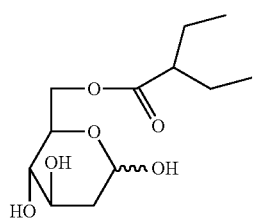

17. The method of claim 1, wherein the compound is

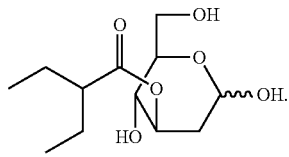 [SMILES: CCC(CC)C(=O)OC1CC(O)OC(CO)C1O]

18. The method of claim 1, wherein the compound is

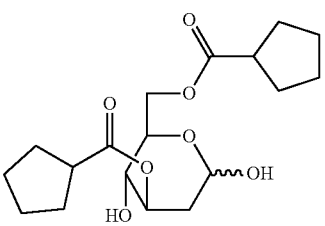

19. The method of claim 1, wherein the compound is

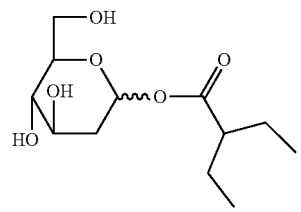

20. The method of claim 1, wherein the compound is

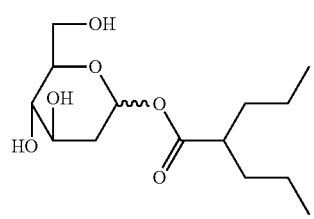

21. The method of claim 1, wherein the compound is

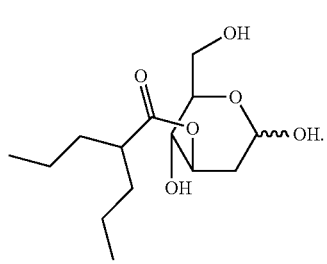 [SMILES: CCCC(CCC)C(=O)OC1CC(O)OC(CO)C1O]

22. The method of claim 1, wherein the compound is

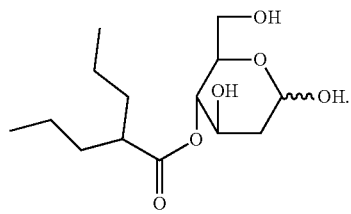

23. The method of claim 1, wherein the compound is

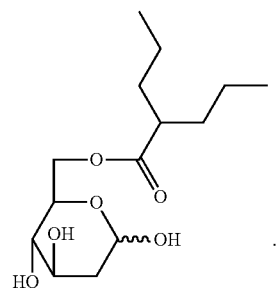

24. The method of claim 1, wherein the compound is

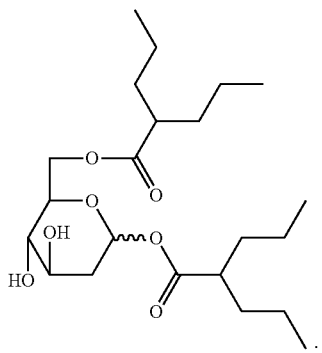

25. The method of claim 1, wherein the compound is

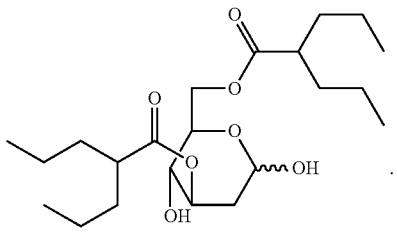 [SMILES: CCCC(CCC)C(=O)OCC1OC(O)CC(OC(=O)C(CCC)CCC)C1O]

26. The method of claim 1, wherein the compound is

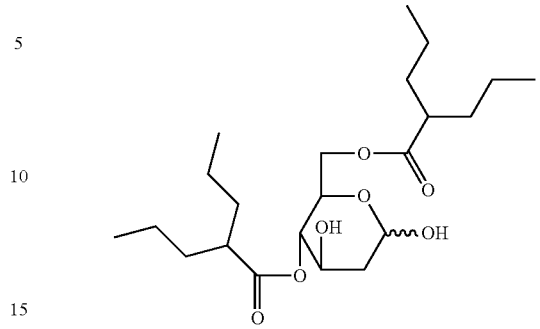

27. The method of claim 1, wherein the proliferative disease is squamous cell carcinoma.

28. The method of claim 1, wherein the proliferative disease is lung adenocarcinoma.

29. The method of claim 1, wherein the one or more compounds of the Formula I are administered with one or more one or more autophagy-inducing agents.

30. The method of claim 29, wherein the authophagy-inducing agent is chosen from Rapamycin is useful as an autophagy-inducing agent, concanavalin A, inhibitors of eEF-2 Kinase Inhibitors and histone deactylase inhibitors.

31. The method of claim 1, wherein the one or more compounds of the Formula I are administered with one or more hypoglycemic agents.

32. The method of claim 31, wherein the one or more hypoglycemic agents are chosen from insulin, alpha-glucosidase inhibitors, sulfonylureas, meglitinides, D-phenylalanine derivatives, biguanides, thiazolidinediones, GLP-1 analogues, and DPP-4 Inhibitors.

* * * * *